United States Patent
Moskovitz et al.

[11] Patent Number: 5,885,291
[45] Date of Patent: Mar. 23, 1999

[54] MINIMALLY INVASIVE SPINAL SURGICAL METHODS AND INSTRUMENTS

[75] Inventors: Peter A. Moskovitz, Washington, D.C.; Scott Boden, Atlanta, Ga.; William F. McKay; Joseph Moctezuma, both of Memphis, Tenn.

[73] Assignee: SDGI Holdings, Inc., Wilmington, Del.

[21] Appl. No.: 939,791

[22] Filed: Sep. 29, 1997

Related U.S. Application Data

[62] Division of Ser. No. 670,351, Jun. 25, 1996, Pat. No. 5,741,261.

[51] Int. Cl.$^6$ .................................................... A61B 17/00
[52] U.S. Cl. ............................................. 606/79; 606/86
[58] Field of Search ................................ 606/79, 80, 81, 606/83, 84, 86, 87, 88, 89, 90

[56] References Cited

U.S. PATENT DOCUMENTS

| | | | |
|---|---|---|---|
| 5,334,194 | 8/1994 | Mikhail | 606/86 |
| 5,374,269 | 12/1994 | Rosenberg | 606/80 |
| 5,380,331 | 1/1995 | Mikhail | 606/86 |
| 5,624,446 | 4/1997 | Harryman, II | 606/86 |

*Primary Examiner*—Michael Buiz
*Assistant Examiner*—Daphna Shai
*Attorney, Agent, or Firm*—Woodard, Emhardt, Naughton, Moriarty & McNett

[57] ABSTRACT

Minimally invasive spinal surgical techniques and tools are provided. The methods include separating the iliocostalis lumborum muscle from the anterior leaf of the thoracolumbar fascia to create a channel from the patient's skin to the intertransverse interval. In one embodiment, the method also includes delivering graft material through the channel to the intertransverse interval. A device according to one aspect of the present invention includes a retraction portion having a flattened plate configured to atraumatically retract tissue to create a working space within an endosurgical site and a curved shaft attached to the retraction portion. The shaft includes a bend having a radius of preferably 160 degrees. A gripping portion is attached to the shaft and is configured for manually gripping and manipulating the device.

20 Claims, 20 Drawing Sheets

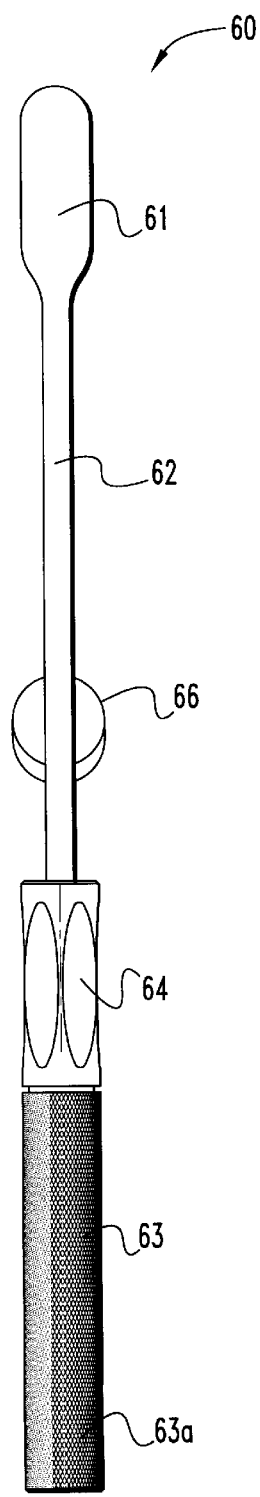
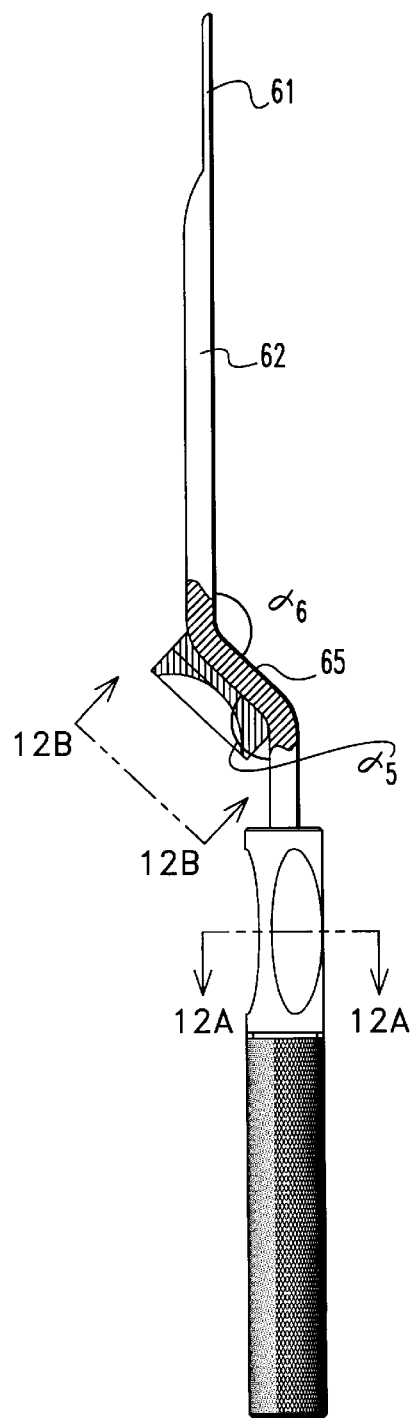
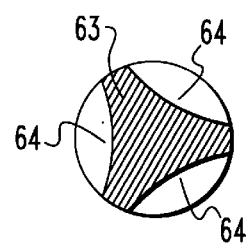
Fig. 12A
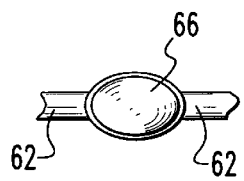
Fig. 12B
Fig. 10
Fig. 11

MINIMALLY INVASIVE SPINAL SURGICAL METHODS AND INSTRUMENTS

This application is a division of application Ser. No. 08/670,351, filed Jun. 25, 1996, now U.S. Pat. No. 5,741,261.

FIELD OF THE INVENTION

The present invention relates to devices, instruments and methods for performing percutaneous minimally invasive spinal surgeries, particularly at locations deep within the body. One specific application of the invention concerns endo-surgical postero-lateral approaches to the intertransverse interval for arthrodesis.

BACKGROUND OF THE INVENTION

Spinal fusion is indicated to provide stabilization of the spinal column for painful spinal motion and disorders such as structural deformity, traumatic instability, degenerative instability, and post-resection iatrogenic instability. Fusion, or arthrodesis, is achieved by the formation of an osseous bridge between adjacent motion segments. This can be accomplished within the disc space, anteriorly between contiguous vertebral bodies or posteriorly between consecutive transverse processes, laminae or other posterior aspects of the vertebrae.

An osseous bridge, or fusion mass, is biologically produced by the body upon skeletal injury. This normal bone healing response is used by surgeons to induce fusion across abnormal spinal segments by recreating spinal injury conditions along the fusion site and then allowing the bone to heal. A successful fusion requires the presence of osteogenic or osteopotential cells, adequate blood supply, sufficient inflammatory response, and appropriate preparation of local bone. This biological environment is typically provided in a surgical setting by decortication, or removal of the outer, cortical bone to expose the vascular, cancellous bone, and the deposition of an adequate quantity of high quality graft material. To provide the best possible patient care, the surgeon is presented with the challenge of surgically accessing the fusion site and providing graft material to the site without causing excessive morbidity and trauma to healthy tissue.

The lumbar spine is of particular interest because of the great number of cases requiring fusion and the difficulty in treating that area. Lumbar spine fusions represent over 95% of the surgical treatment for mechanical back pain and spinal instability associated with trauma or neurological pain. The lumbar region is a challenging area for fusion because of the great mobility and mechanical stresses. Unfortunately, solid union of the effected vertebrae can not always be achieved by traditional methods. Each of the three major lumbar fusion procedures, interbody fusion, posterior fusion and intertransverse process fusion have their share of complications and pseudoarthrosis.

Of the three, intertransverse arthrodesis has been preferred because it is the most reliable method for treating deformity, instability, or painful lumbar segments. This procedure provides high rotatory and translatory stability with sufficient rigidity. Furthermore, the risk of pseudoarthrosis is low probably due to the large contiguous surface area for grafting provided by the transverse processes. In spite of its popularity and relative success, therapeutic intertransverse arthrodesis still suffers from three primary weaknesses: 1) the incidence of nonunion can be as high as 35%; 2) iliac bone graft donor site morbidity occurs in up to 30% of patients; and 3) extensive dissection of paraspinal muscles at and adjacent to the levels being fused may cause fusion disease.

Either the inter-muscular or midline approaches have been most commonly used for intertransverse process arthrodesis. In the midline approach shown in FIG. 1, muscle stripping begins at the spinous process S and proceeds across the laminae M, over the capsule of the facet f joint, down the lateral wall of the superior facet process f and out to the tip of the transverse process P. The inter-muscular approach, which is depicted in FIG. 2 begins with a subperiosteal dissection of bone at the lateral border of the superior facet process f. In both approaches, the posterior primary ramus of the segmental nerve root must be divided along with the vascular tree which accompanies it. Pressure necrosis of the paraspinal muscles can result from prolonged retraction for the deep exposure. In both approaches the incision is long and extensive muscle stripping is required at least one half level above and below the level of the intended fusion to mobilize the thick muscle mass.

These procedures, like most open spinal surgeries, require a recovery room time of several hours and several weeks of post-operative recovery time due to the use of general anesthesia and the destruction of tissue during the surgical procedure. The long incision, extensive muscle stripping, prolonged retraction of tissues, denervation and devascularization of tissue of these traditional surgical procedures cause significant trauma to the intervening tissues. Sometimes this trauma leads to persistent pain and impairment which has been labeled "fusion disease." In some cases, these invasive procedures frustrate the surgeon's purpose by causing fusion disease which can be more severe than the condition leading to the surgical intervention. Not surprisingly, many patients are reluctant to seek surgery as a solution to pain from spinal conditions because of the severe postoperative pain associated with the muscle dissection and the risks of open and prolonged spinal surgery.

Less invasive alternatives such as arthroscopic techniques have been developed to reduce pain, post-operative recovery time and the destruction of healthy tissue. Orthopedic surgical patients have particularly benefited from minimally invasive surgical techniques. The site of pathology is accessed through portals rather than through a large open incision thus preserving the integrity of the intervening tissues. These minimally invasive techniques also often require only local anesthesia. The avoidance of general anesthesia and significant tissue trauma reduces post-operative recovery time and the risk of complications. Many of these procedures are performed on the shoulder and knee on an outpatient basis with great success.

Minimally invasive surgical techniques are particularly desirable for spinal applications because of the need for access to locations deep within the body and the danger of damage to intervening vital tissues. In order to reduce the post-operative recovery time and pain associated with spinal and other procedures, various micro-surgical techniques have been developed. For example, in micro-surgical discectomies, the disc is accessed by cutting a channel from the surface of the patient's back to the disc through a small incision. An operating microscope or loupes is used to visualize the surgical field. Small diameter micro-surgical instruments are passed through the small incision and between two laminae and into the disc. The intervening tissues are disrupted less because the incision is smaller. Although these micro-surgical procedures are less invasive, they still involve some of the same complications associated with open procedures, such as injury to the nerve root and dural sac, perineural scar formation, reherniation at the surgical site and instability.

Laparoscopic and thoracoscopic techniques have been developed for anterior approaches to the thoracic and lumbosacral spine. Sofamor Danek Group markets instruments used in a laparoscopic bone dowel technique for anterior interbody fusions as an alternative to standard open anterior retroperitoneal approaches. In U.S. Pat. No. 5,195,541, Obenchain discloses a video assisted method of performing a laparoscopic discectomy using an anterior approach. These techniques typically use carbon dioxide gas as the visualization medium. Other viable alternative for lumbar procedures are needed, however, because the anterior approach is not always indicated. For example, the lumbar spine is not easily accessible anteriorly due to the danger to the great vessels and the immobility of the psoas muscle. There are also risks of complications such as bowel perforation and trauma to the ureters or the sympathetic plexus. Adhesions due to previous abdominal operations may also limit the usefulness of the anterior approach.

U.S. Pat. No. 4,545,374 to Jacobson discloses a percutaneous lumbar discectomy using a lateral approach under fluoroscopic X-ray. The advantage of this procedure is that the lateral approach does not intersect bone, nerves, blood vessels, major back support muscles or ligaments which would otherwise have to be cut or retracted. This procedure is limited because it does not provide direct visualization of the work site and both the patient and the surgeon are exposed to radiation. Although the patent discloses that the procedure is normally performed in about fifteen minutes, the total exposure time for the surgeon could be significant over a period of time. Furthermore, the patient may be exposed for a longer period of time if the surgeon is relatively inexperienced with this technique or if complications arise.

Other procedures have been developed which include arthroscopic visualization of the spine and intervening structures. U.S. Pat. Nos. 4,573,448 and 5,395,317 to Kambin disclose percutaneous decompression of herniated discs with a posterolateral approach. Fragments of the herniated disc are evacuated through a cannula positioned against the annulus. The '317 Kambin patent discloses a biportal procedure which involves percutaneously placing both a working cannula and a visualization cannula allowing simultaneous visualization and suction, irrigation and resection in disc procedures. The posterolateral approach is employed for discectomy to avoid the need for laminectomy. In U.S. Pat. Nos. 5,171,279 and 5,357,983, Matthews discloses percutaneous discectomy and subcutaneous suprafascial internal fixation methods. U.S. Pat. No. 5,439,464 to Shapiro discloses a method and instruments for performing arthroscopic spinal surgeries such as laminectomies and fusions with a mid-line or medial posterior approach using three cannulae each inserted through a separate incision.

While the development of these spinal procedures is a major step towards reducing recovery time because they require less muscle dissection, these procedure still suffer from many of the trauma-inducing disadvantages of previous spinal surgery techniques and tools. One disadvantage is that the cannulae are inserted through stab wounds in imprecise locations. Although the devices are designed to reduce tissue trauma by pushing past the muscle with a cutting or tissue moving end, the cannulae are still inserted through tissue and muscle to arrive at the working space. In most cases, nerve retraction is still required. Furthermore some of these procedures also require a gas or fluid maintained working space.

Fluid is required in some prior procedures to maintain the working space for proper function of optics fixed within a prior art cannula and inserted percutaneously. Irrigation, or the introduction of fluid into the working space, can often be logistically disadvantageous and even dangerous to the patient for several reasons. The introduction of fluid into the working space makes hemostasis more difficult and may damage surrounding tissue. The fluid environment can also make drilling difficult due to cavitation. The requirement for a fluid environment generally increases expenses associated with the surgery and adds to the complexity of the surgery, due in part to the relatively high volume of fluid required.

After the first challenge of accessing fusion site is addressed, the second challenge is to promote bone growth at the fusion site without causing morbidity or trauma to healthy tissues. Bone graft materials are often used to promote spinal fusions. In order to effect solid bone bridging between two widely separated bones, the graft material must: 1) prevent ingrowth of fibrous tissue with a continuous layer of sufficient bulk; 2) provide a scaffold for the elaboration of bone matrix (osteo-conductive property); and 3) stimulate pleuripotential tissues to produce bone matrix and deposit thereon calcium-phosphate crystals to form bone (osteo-inductive property).

Unfortunately, the use of bone graft presents several disadvantages. Autograft, bone material surgically removed from the patient, can be undesirable because it may not be available in sufficient quantities. The structural integrity of the donor site can be compromised by the donor surgery, particularly when large amounts of graft are required. Prior arthrodesis operations can exhaust a patient's accessible supply of suitable autogenous bone. The donor surgery is traumatic to healthy tissue and increases the risk of infection and blood loss. Ironically, some patients complain that the graft harvesting surgery is more painful than the fusion surgery or the pain leading to the procedure. These complications are aggravated for lumbar fusions in which larger amounts of graft material are required.

Allograft material, which is obtained from donors of the same species, is more readily obtained. However, allografts can be disadvantageous because of disease transmission, immune reactions and religious objections. Furthermore, allogenic bone does not have the osteoinductive potential of autogenous bone and therefore may provide only temporary support, leading to pseudoarthrosis and eventual collapse of the disc space.

Bone morphogenetic proteins (BMPs) have been found to significantly reduce the time required to achieve fusion. Several recombinant human BMPs (rhBMPs) are in various stages of development and are promising bone graft substitutes. The use of recombinant BMPs will conceivably reduce recovery time by speeding the rate of bone growth and solve the problems associated with autograft and allograft, such as disease transmission, lack of osteoinductivity, immunoreactivity, as well as morbidity and trauma to a donor surgical site.

The use of any graft material requires caution. For example, when spinal fusion through the midline approach is combined with decompression or laminectomy of the spinal canal, any contaminant of one tissue space may cross-contaminate the other. Bone graft materials, in general, pose the risk of mechanical or iatrogenic complications when introduced into the epidural space. Infection in any area of the midline wound can spread to the full extent of the dissection or beyond. The safety of using BMPs in such procedures has not yet been established. It is unknown what the effect of such proteins will have in the spinal canal, intra-pleural or intra-peritoneal cavities, or retroperitoneum. Certainly there is a possibility of such complications as adhesions, arachnoiditis and retroperitoneal fibrosis.

Two major issues face surgeons in arthrodesis surgeries: exposure of the segments to be fused without causing fusion disease or other complications; and, the safety, efficacy and supply of graft materials. Therefore, a need has remained for surgical techniques which avoid the tissue trauma associated with open spinal surgery as well as risks and limitations associated with endoscopic surgery. A need has also remained for intertransvrerse process fusion procedures which do not cause fusion disease or other complications. A need has also remained for surgical procedures which safely use recombinant bone morphogenetic proteins in spinal fusions.

SUMMARY OF THE INVENTION

Briefly describing one aspect of the invention, there is provided minimally invasive spinal surgical techniques and tools. The methods include separating the iliocostalis lumborum muscle from the anterior leaf of the thoracolumbar fascia to create a channel from the patient's skin to the intertransverse interval. In one embodiment, the method also includes delivering graft material through the channel to the intertransverse interval. In one specific embodiment the channel has a diameter of about 2.5 cm. A device according to one aspect of the present invention includes a retraction portion having a flattened plate configured to atraumatically retract tissue to create a working space within an endosurgical site and a curved shaft attached to the retraction portion. The shaft includes a bend subtending an angle of at least about 120 degrees, preferably about 160 degrees. A gripping portion is attached to the shaft and is configured for manually gripping and manipulating the device.

One object of the present invention is to provide persons suffering from diseases and injuries of the lumbar spine an endo-surgical alternative to traditional open lumbar spinal arthrodesis. Another object is to reduce morbidity, hospital stay, rehabilitation and cost, both financial and human. Still another object of this invention is to reduce the morbidity of lumbar spine arthrodesis by eliminating the surgical harvesting of bone graft.

One advantage of this invention is that it allows access to the intertransverse interval without major muscle dissection and nerve retraction. Another advantage is that this invention avoids the conceivable risks of bone morphogenetic proteins.

BRIEF DESCRIPTION OF THE DRAWINGS

FIG. 10 is a top elevational view of an endosurgical elevator provided by this invention.

FIG. 11 is a side elevational view of the elevator shown in FIG. 10.

FIG. 12A is a cross-sectional view of the elevator shown in FIGS. 10 and 11 taken along lines A—A.

FIG. 12B is a cross sectional view of the elevator shown in FIGS. 10 and 11 taken along lines B—B.

DESCRIPTION OF THE PREFERRED EMBODIMENTS

Figure 1:
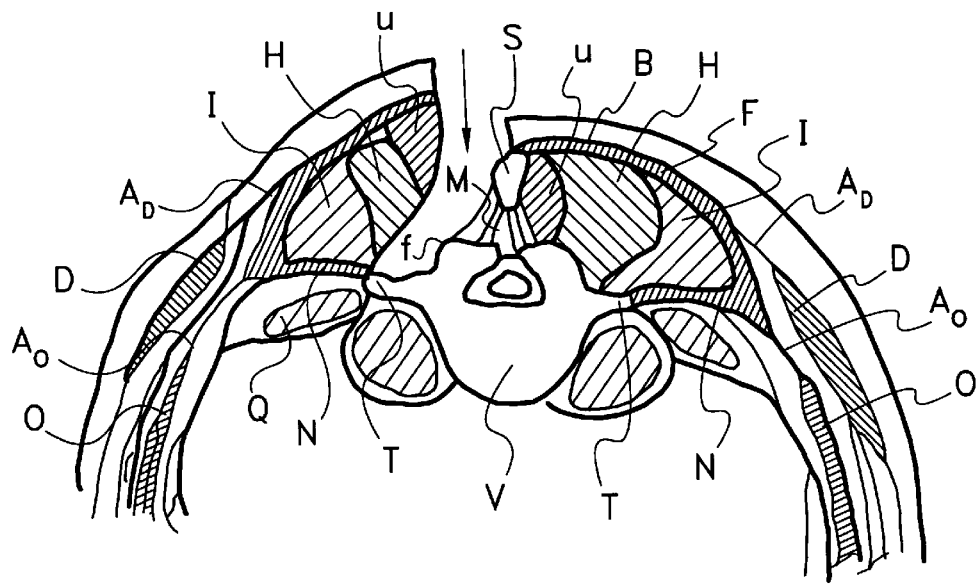
FIG. 1 is a transverse section of the human body showing the midline approach to the intertransverse interval.
Figure 2:
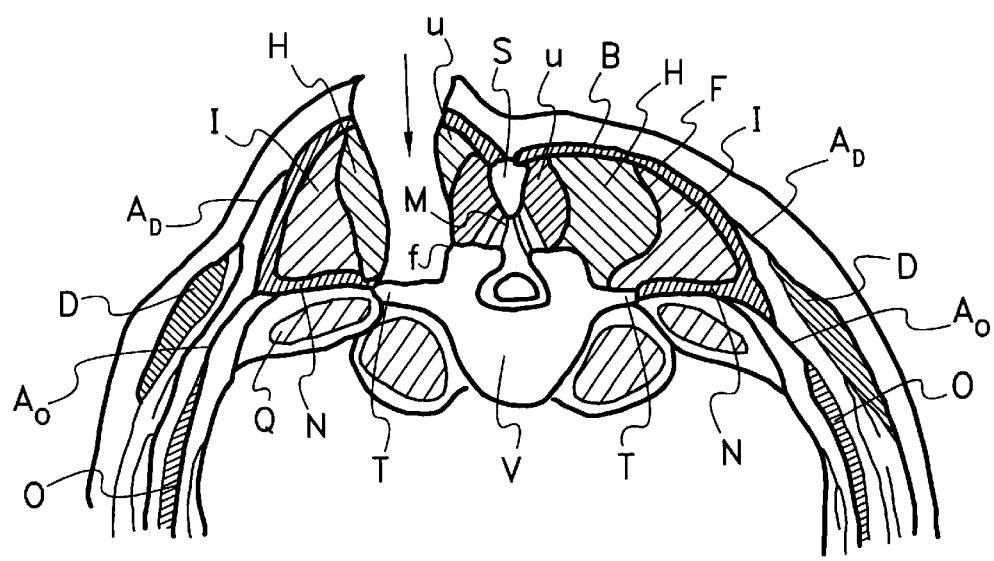
FIG. 2 is a transverse section of the human body showing the inter-muscular approach to the intertransverse interval.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides devices and surgical procedures for minimally invasive postero-lateral approaches to an intertransverse interval. This invention is based upon the discovery that the lumbar region can be accessed posterolaterally between the major back muscles without the need for major muscle dissection. Instruments can be inserted between natural muscle planes to reduce trauma and fusion disease. Unlike other traditional spinal surgical procedures, this approach extends between and not through major back muscles. This technique also avoids significant muscle and nerve retraction and does not traverse vital structures, viscera, major vessels or neurologic elements. The methods also preserve a natural tissue barrier between the fusion site and the epidural space to prevent the debilitating effects of expulsion of the fusion implant, seepage of osteogenic factor or spread of infection from the fusion site and into the spinal canal. Advantageously, this avoids the trauma and morbidity associated with fusion disease and minimizes any danger of migration or inappropriate action of BMPs. Furthermore, the use of recombinant BMPs with this invention also avoids a donor surgery for autograft or the risks of allograft.

Figure 3:
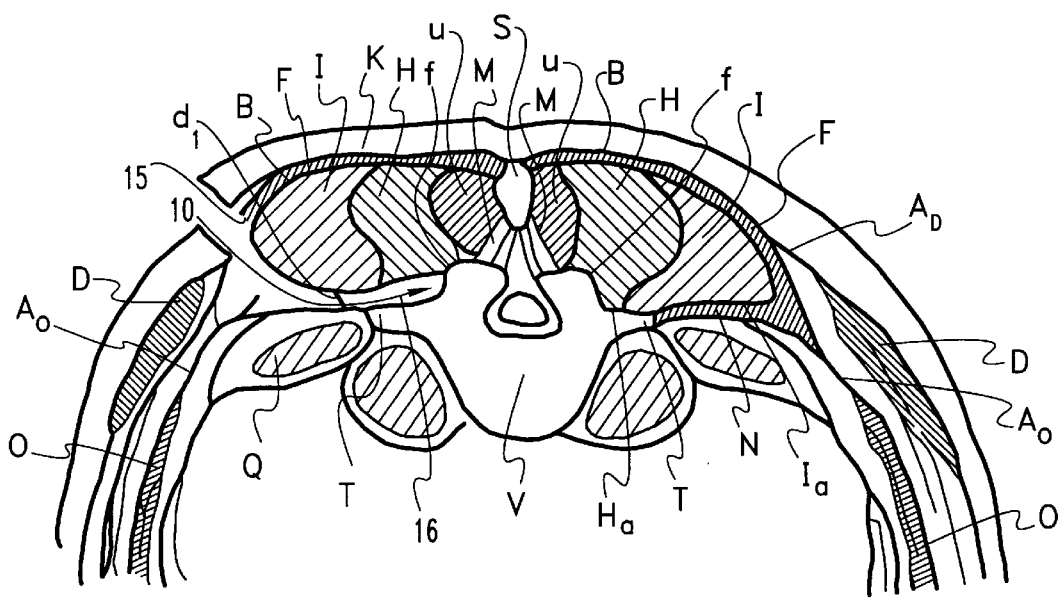
FIG. 3 is a transverse section of the human body showing one approach of this invention to the intertransverse interval.
Figure 4:
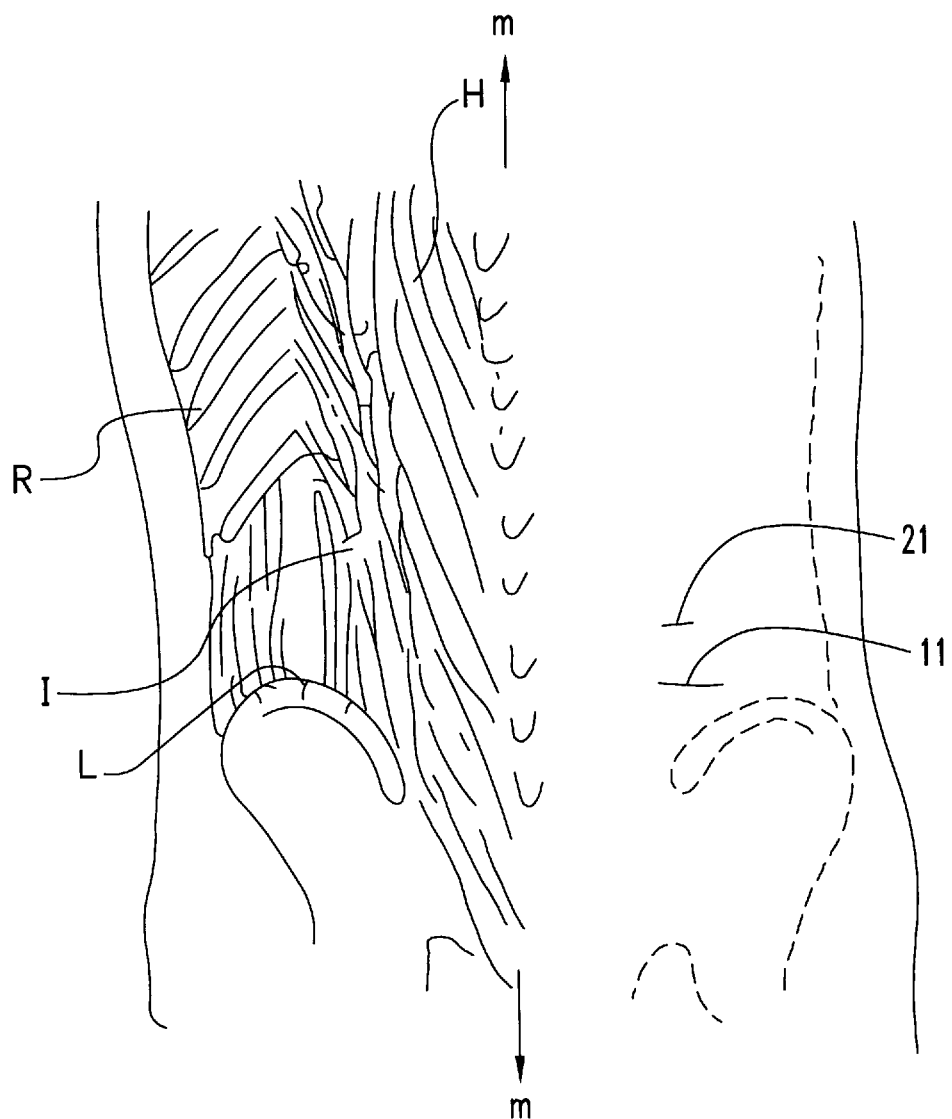
FIG. 4 is a partial longitudinal section of the human body showing incisions for the embodiment shown in FIGS. 3 and 19.

The feasibility of this approach capitalizes on the anatomy of the back, in particular the filmy areolar plane between the erector spinae muscles and the thick thoracolumbar fascia F. Referring to FIGS. 1–4, the fascia F is thick and begins at the spinous processes S of the lumbar vertebrae V, extends laterally to the aponeurosis $A_O$ of the internal oblique O and transverses, reflecting acutely antero-medially along the anterior surface $I_A$ of the iliocostalis muscle I, then attaches to the tips of the transverse processes P. The quadratus lumborum muscle Q lies directly anterior to the anterior portion N of the thoraco-lumbar fascia F. The aponeurosis $A_D$ of the latissimus dorsi muscle D is confluent with the posterior portion B of the thoraco-lumbar fascia F at the spinous processes S, but is a separate layer as the thoracolumbar fascia F reflects anteriorly. The multifidus muscles U originate laterally at the articular facets f and insert medially on the spinous processes S of the vertebrae V located two to four levels superiorly. The longissimus thoracic muscle H originates from the transverse processes P and insert on the transverse processes P several levels above. As shown in FIG. 4, the iliocostalis muscles I are the most laterally placed of the paraspinal muscles and originate on the wing of the ilium L and insert at the angle of the lower five ribs R. The iliocostalis I is contained within the compartment of the thoraco-lumbar fascia F but has no attachment to the fascia F and is easily separated from it. A working space can be created between the major paraspinal muscles and the thoracolumbar fascia for small scopes and instruments with relatively minimal trauma.

Figure 5:
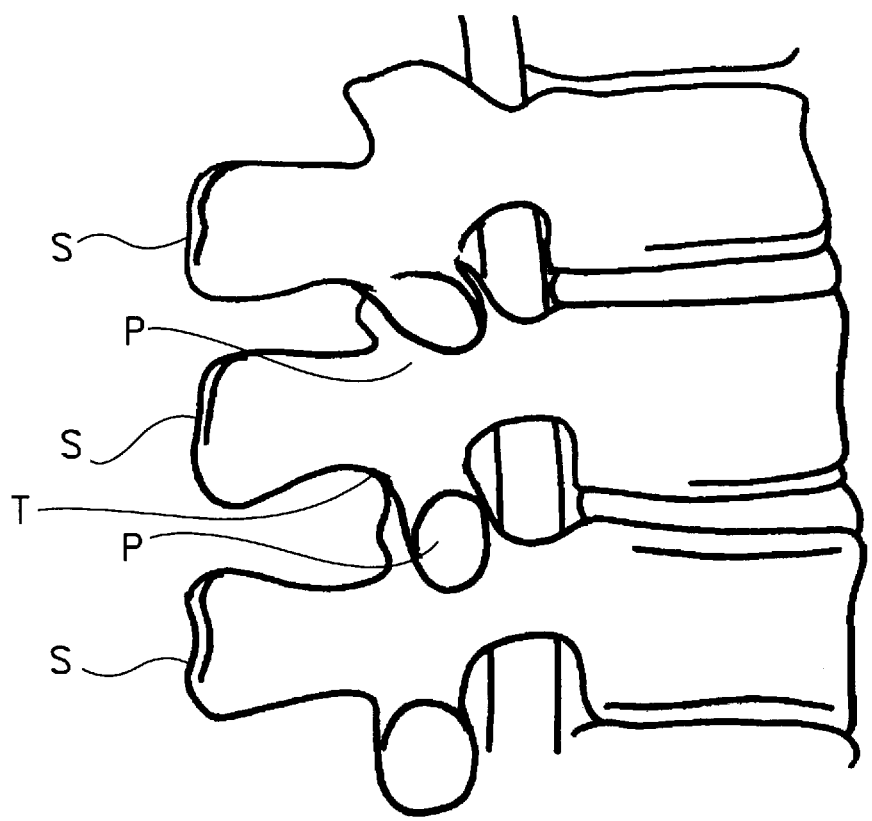
FIG. 5 is a side elevational view of a segment of three human lumbar vertebrae.

The present invention provides techniques and tools which exploit these features of anatomy for minimally invasive approaches to the spine. In one embodiment, a method for approaching the intertransverse process interval T (shown in FIG. 5) includes separating the iliocostalis lumborum muscle I from the anterior leaf N of the thoracolumbar fascia F to create a primary portal or channel 10 from the patient's skin K to the intertransverse interval T as shown in FIG. 3. Preferably, a first portion 15 of the channel 10 has a major diameter $d_1$ of less than about 4.0 cm. Most preferably the first portion 15 has a diameter $d_1$ of about 2.5 cm.

In some embodiments of this invention, the methods of this invention can be used for arthrodesis of an intertransverse interval T in the lumbar spine. Discectomy and decompression can be first performed using known techniques, preferably minimally invasive techniques. Advantageously, the arthrodesis procedures of this invention do not require that the patient be repositioned after posterior midline spinal canal surgery. According to the methods of this invention bone graft and graft substitutes can be safely implanted in the intertransverse interval without risk of mechanicxal or biological invasion of the epidural space even after laminectomy. The methods safely approach the interval without violating the integrity of a tissue plane separating the channel from the laminectomy site. The tissue plane or barrier provided by the posteromedio attachments of the longissimus thoracic H at the superior articular facet f of the adjacent vertebrae protects the spinal canal from the graft implant if it is expelled or if osteogenic factors seep from the implant.

In the practice of one specific embodiment of this invention, the patient is placed in the prone position under anesthesia of choice. Any suitable anesthesia is contemplated. Preferably, a local anesthesia will be used in combination with a sedative. One advantage of this invention is that the risks and long recovery periods of general anesthesia can be avoided.

After the patient has been properly positioned and anesthetized, a first primary transverse incision 11 (FIG. 4) is made through the skin K approximately 10 cm from the midline at the level of the spinous process S cephalad to the fusion site which is preferably at intertransverse interval T. The primary incision 11 is large enough to accept a cannula but preferably less than about 4.0 cm in length and most preferably about 2.5 cm in length. The incision 11 is centered over the border of the reflection of the thoracolumbar fascia F. This reflection is palpable at the edge of the topological prominence of the iliocostalis muscle I.

Figure 6:
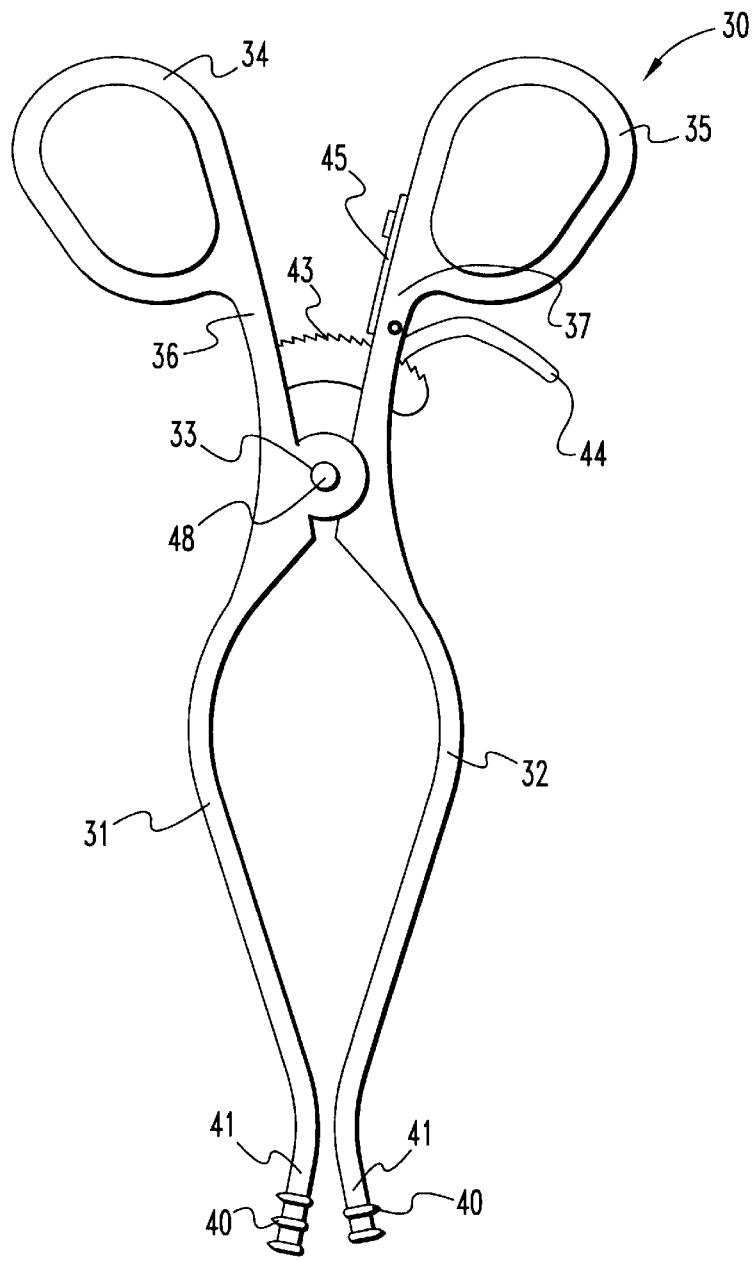
FIG. 6 is a side elevational view of a self-retaining retractor provided by this invention.
Figure 7:
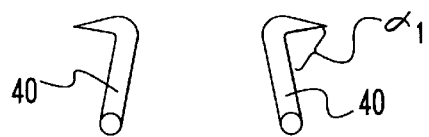
FIG. 7 is an end elevational view of the retractor shown in FIG. 6.

The skin is then retracted with a self retaining retractor, preferably with a retractor 30 such as depicted in FIGS. 6 and 7. The subcutaneous fat is preferably dissected to expose the posterior leaf B of the thoracolumbar fascia F. A deeper primary incision (not shown) can then be made through the thoracolumbar fascia F to expose the iliocostalis I. The deeper primary incision is preferably centered beneath the first primary incision 11 and made in the line of the fibers of the fascia F. The length of the deeper primary incision is preferably no longer than the first primary incision 11 and is most preferably about 2.5 cm.

Figure 13:
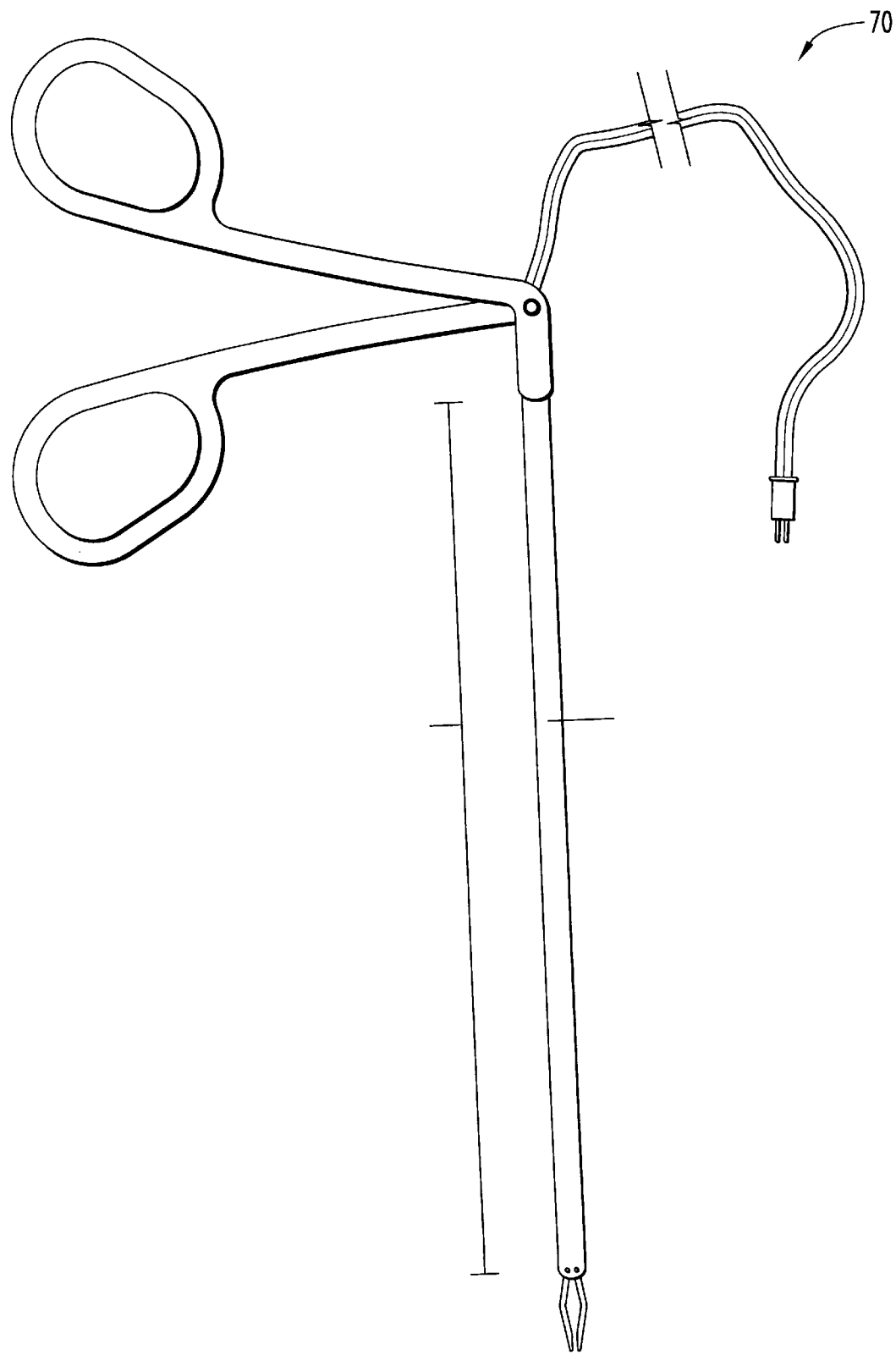
FIG. 13 is a side elevational view of an endosurgical bipolar cautery device provided by this invention.

A primary portal or working channel 10 is created through the first transverse incision 11 and the second primary incision to the intertransverse interval T. This is done by inserting an endosurgical retractor, such as the device 50 depicted in FIGS. 8 and 9, between the muscles and the fascia F. The first portion 15 of the channel 11 extends between the lateral border of the iliocostalis I and the anterior leaf N of the fascia F. To accomplish this, the lateral border of the iliocostalis I can be dissected from the anterior leaf N of the thoracolumbar fascia F. The iliocostalis I may also be dissected from the fascia F medially about 0.5 cm dorsal to the junction of the transverse process P and the lateral cortex of the cephalad articular facet f. Dissecting and elevating the fascia F from the anterior border Ia of the iliocostalis I and the anterior border H a of the longissimus thoracic H muscles creates a second portion 16 of the channel 10. The posteromedio attachment of the longissimus thoracic muscle H to the superior articular facet f is preserved. These muscles provide a natural tissue barrier between the fusion site and the epidural space. Preferably the intertransverse process membrane (not shown) is also medially dissected to the hiatus of the posterior rami of the segmental nerve and vessels. This is most conveniently accomplished with an endosurgical elevator 60 such as the one depicted in FIGS. 10–12B. Hemostasis can be effected with an endosurgical bipolar cautery such as the device 70 depicted in FIG. 13.

Figure 14:
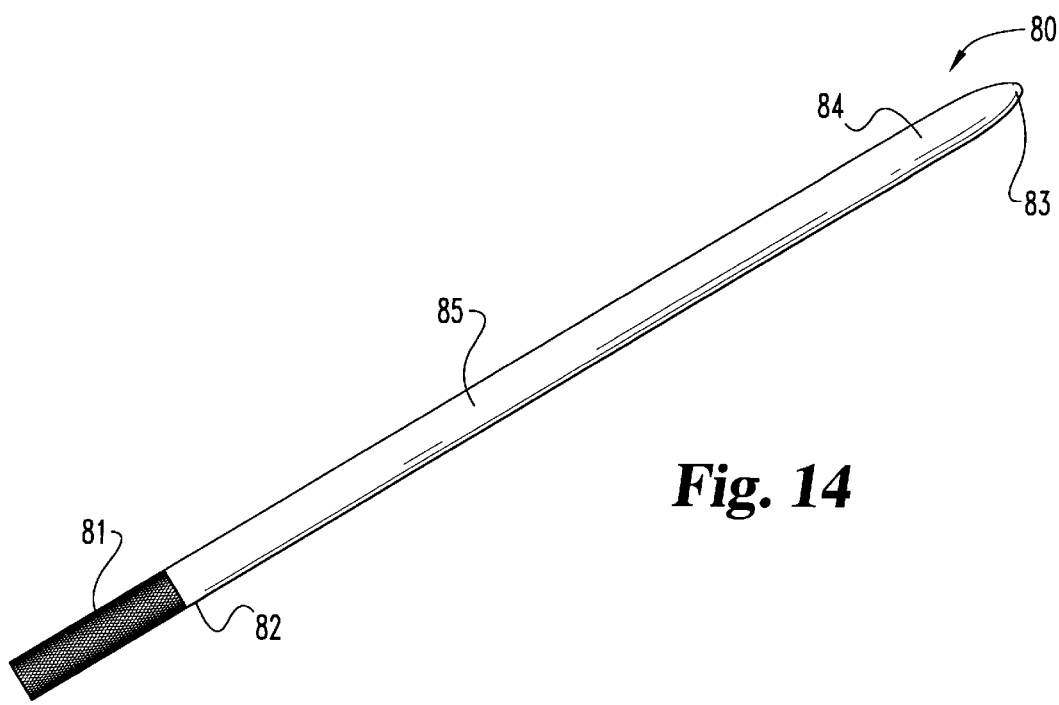
FIG. 14 is a side elevational view of an endosurgical blunt probe provided by this invention.

Digital palpat will identify the cephalad and the caudal transverse processes P. A probe or obturator such as the endosurgical blunt probe 80 shown in FIG. 14 can be inserted between the transverse processes P. This probe 80 includes a shaft 85 having a knurled gripping portion 81 at one end 82 and a bullet tip 83 at an opposite end 84. Preferably, the identity of the intertransverse process interval T will also be confirmed by X-ray. A speculum such as the self-retaining endosurgical speculum 90 shown in FIGS. 15 and 16 can be inserted between the iliocostalis I and the anterior thoracolumbar fascia F to create a working space or the channel 10. A cannula can then be inserted into the channel 10. The cannula may be either a working or a visualization cannula such as the sheath 103 depicted in FIG. 18 for the endoscope 100 shown in FIG. 17.

Alternatively, the working channel 10 to the intertransverse interval T can be created in the following manner. The first portion 15 of the channel 11 is created by developing the areolar plane between the iliocostalis I and the anterior leaf N of the thoracolumbar fascia F. This is preferably accomplished by digital dissection to the junction of the iliocostalis I and longissimus thoracis H. Digital dissection will identify the cephalad and caudal transverse processes P. Preferably, the identity of the transverse process interval T will be confirmed by X-ray. For this purpose, a probe or obturator such as the endosurgical blunt probe 80 shown in FIG. 14 can be inserted between the transverse processes P.

The second portion 16 of the channel 10 is created by dissecting the longissimus thoracic muscle H from its attachments to the thoracolumbar fascia F, the transverse processes P and the intertransverse process membrane (not shown). Because the longissimus thoracis muscle H inserts in a cephalad direction, the surgeon will preferably begin this dissection of the muscle H from the caudal transverse process P. Most preferably, this dissection is performed using a combination of palpation, with the surgeon's index finger controlling the tip of the target transverse process P, and direct visualization. The attachment of the longissimus thoracic H to the superior articular facet f of the adjacent vertebrae is preserved.

Figure 8:
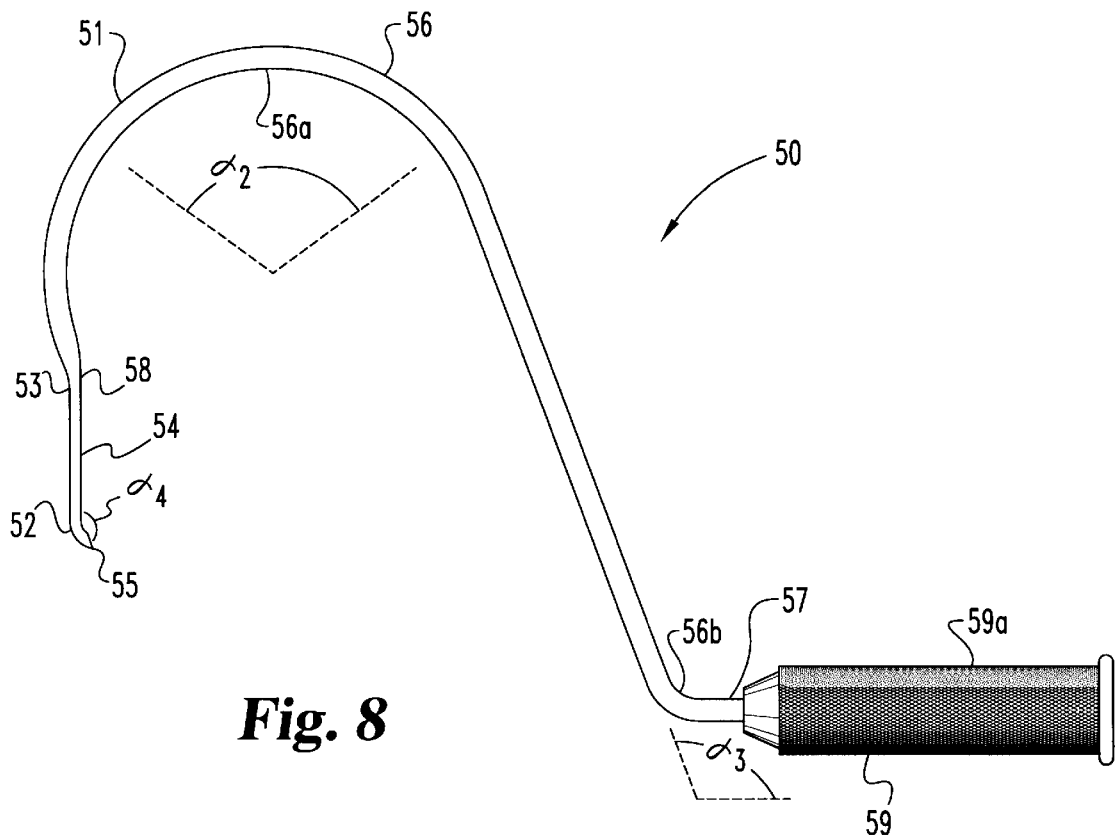
FIG. 8 is a side elevational view of an endosurgical retractor provided by this invention.
Figure 9:
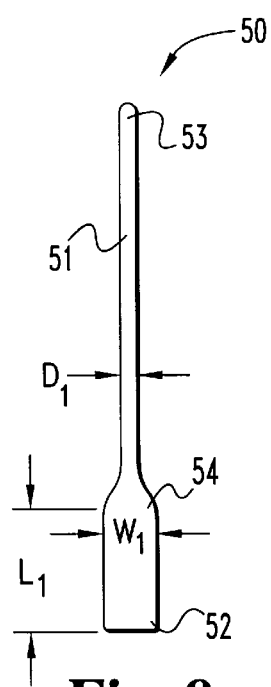
FIG. 9 is a front elevational view of the retraction portion of the retractor shown in FIG. 8.
Figure 17:
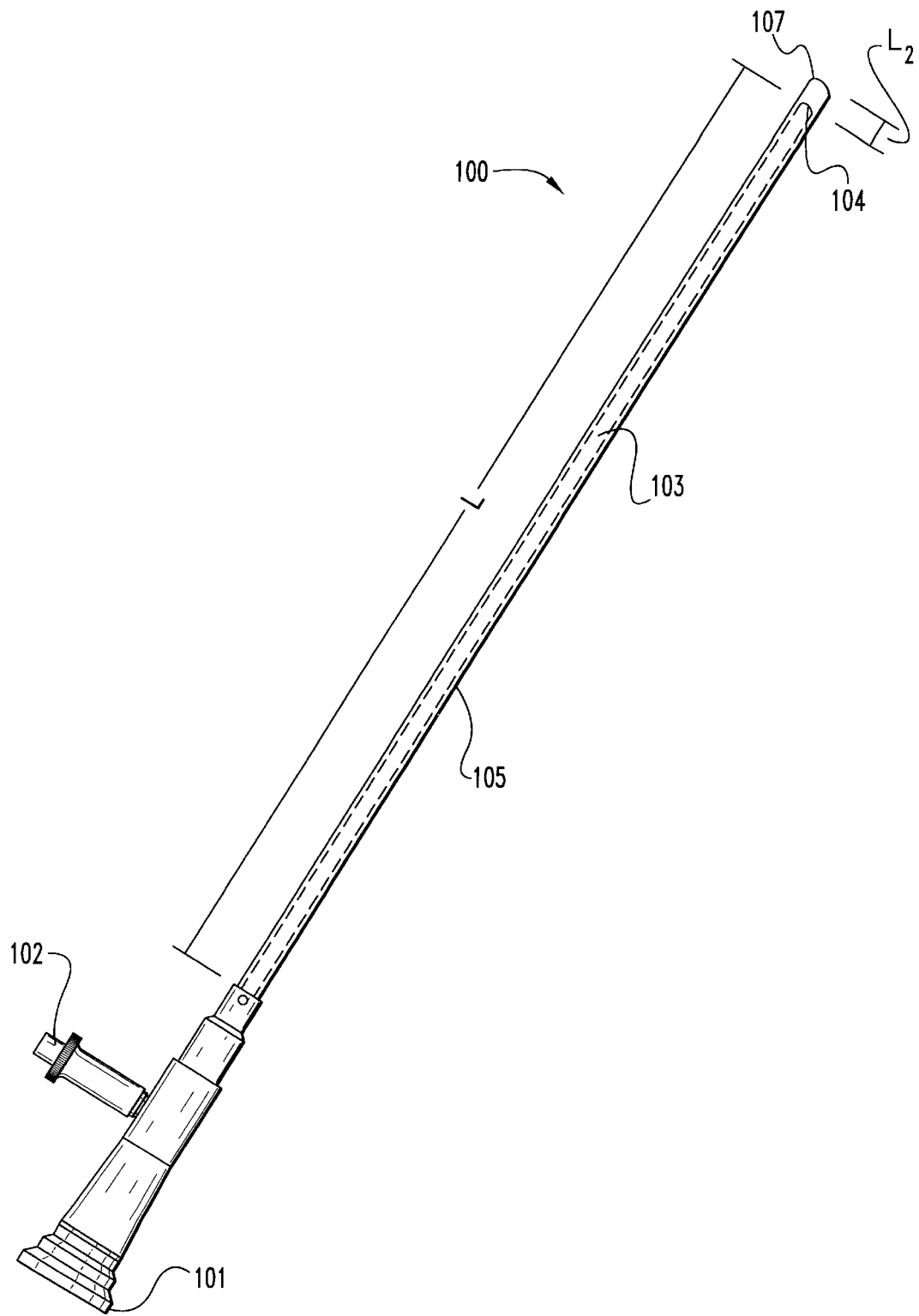
FIG. 17 is a side elevational view of an endoscope provided by this invention.
Figure 18:
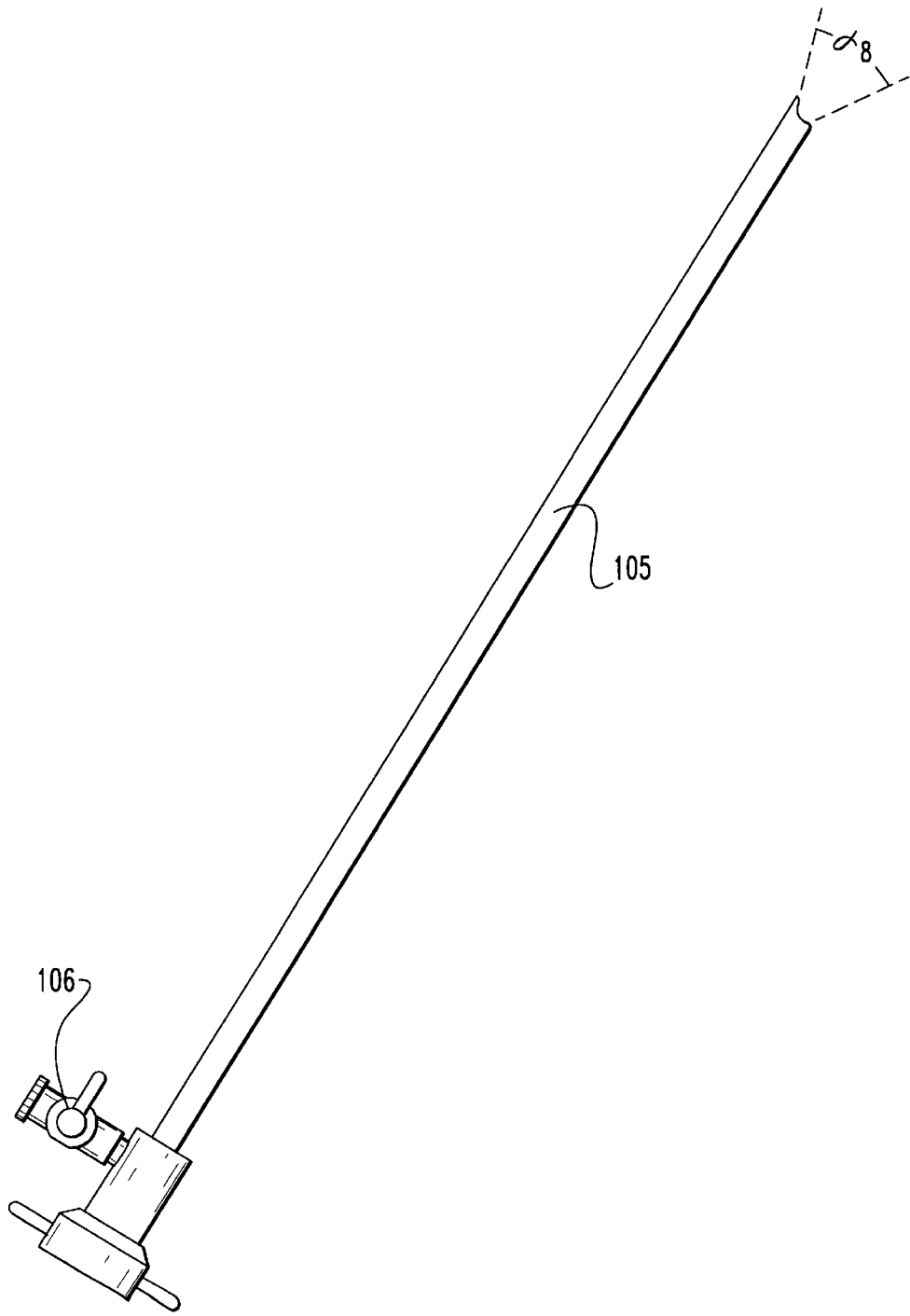
FIG. 18 is a side elevational view of a sheath for use with the endoscope shown in FIG. 17.

Direct visualization of the plane of dissection may be accomplished by inserting a device into the channel 10. In one embodiment an endosurgical retractor 50 depicted in FIGS. 8 and 9 is inserted between the muscles and the fascia F. The ilicostalis I and longissimus H muscles are retracted dorsally to create the working space. An endoscope such as the scope 100 depicted in FIG. 17, protected by a sheath 105 shown more clearly in FIG. 18, is inserted into the working space to visualize the dissection which develops the second portion 16 of the primary portal 10. The second portion 16 completely exposes the transverse processes P, the junction J of the processes P and an anterior portion fa of the superior facet processes f, and the intertransverse process membrane (not shown). Preferably the intertransverse process membrane is dissected medially to the hiatus of the posterior rami of the segmental nerve and vessels. This is most conveniently accomplished with an endosurgical elevator 60 such as the one depicted in FIGS. 10–12B. Hemostasis is effected with an endosurgical bipolar cautery such as the device 70 depicted in FIG. 13.

In some embodiments, an accessory portal 20 (FIGS. 4 and 19) is created through a small secondary incision 21 for decortication or visualization after the transverse processes P are exposed. The incision 21 is preferably about 0.5 cm in length and located about 3 cm from the midline m. When the incision 21 is about 0.5 cm it can be closed with a single skin suture. A blunt obturator or probe can then be passed through the incision 21 and between the fibers of the longissimus thoracic muscle H and into the channel 10. The direction of the obturator can be guided by digital palpation through the wound at the primary incision 11. Once the obturator is safely in the channel 10 and resting against a transverse process P, a sheath can then be passed over the obturator and the obturator removed. The sheath may be either a visualization sheath or a decorticating burr sheath.

The instrument of choice, either an endoscope or burr, is then passed into the sheath. For decortication, the accessory portal 20 permits the removal of bone from the transverse processes P and the superior facet f process without risk of the burr skipping and injuring adjacent soft tissue. Also, the orthogonal position of the endoscope and the decorticating burr gives better stereognosis to the surgeon. During insertion of graft material into the intertransverse process interval T, the surgeon may elect visualization through the accessory portal 20 when the primary portal 10 is obscured by the graft material.

Figure 19:
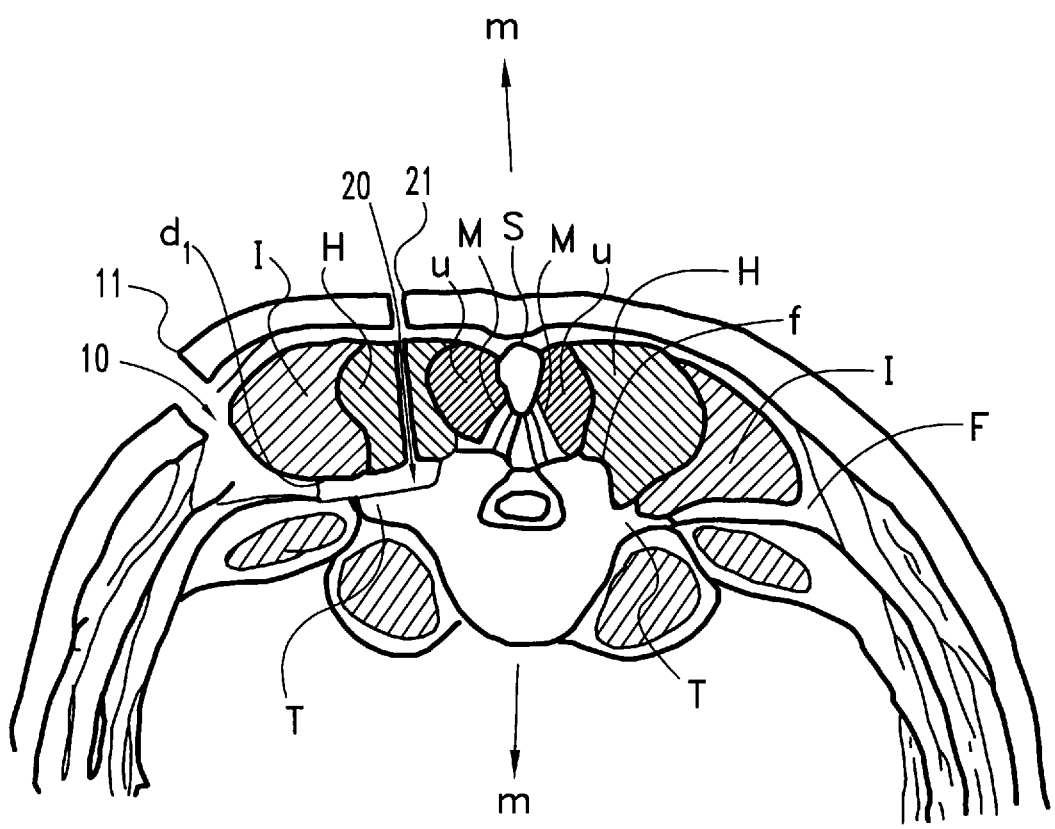
FIG. 19 is a transverse section of the human body showing the approach of FIG. 3 with an accessory portal.

Of course, the accessory portal 20 may not be necessary if a cannula is used which supports both visualization and working instruments. The accessory portal 20 is either caudal or cephalad to the primary incision 11 depending on the handedness of the surgeon and the cutting direction (clockwise or counterclockwise) of the decorticating burr. In one specific embodiment, the accessory portal 20 depicted in FIG. 19 is created through a 0.5 cm secondary incision 21 made 3–4 cm from the midline, 4–5 cm cephalad to the primary incision 11. The secondary portal 20 preferably has a diameter of about 0.5 cm.

This invention also contemplates arthrodesis of multiple motion segments. For fusion across two motion segments, the primary incision 11 is made over the middle transverse process. Where fusion of three or more motion segments is required, multiple primary incisions and portals are required.

Finally, a graft implant or material is placed in the intertransverse process interval T to promote fusion. Preferably, this is accomplished using an endosurgical graft delivery assembly 110 provided by this invention and depicted in FIGS. 20 and 21. Graft material is placed in the cannula 111 as chunks, paste, particles, or strips. The graft material is delivered directly to the base of the transverse process P and distributed to the intertransverse process interval T. In one embodiment, this is accomplished using the endosurgical elevator 60.

Any suitable graft implant or material is contemplated. Autograft, allograft, xenograft, synthetic and natural bone graft substitutes, such as ceramics and polymers, and osteogenic compositions can all be used to promote fusion in this invention. The term osteogenic composition used here means virtually any material that promotes bone growth or healing including natural, synthetic and recombinant proteins, hormones and the like.

Figure 22:
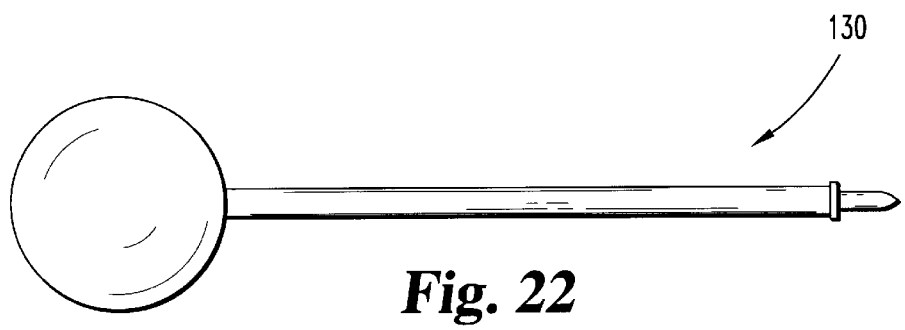
FIG. 22 is a side elevational view of an awl provided by this invention.
Figure 24:
FIG. 24 is a side elevational view of guide pin provided by this invention.
Figure 25:
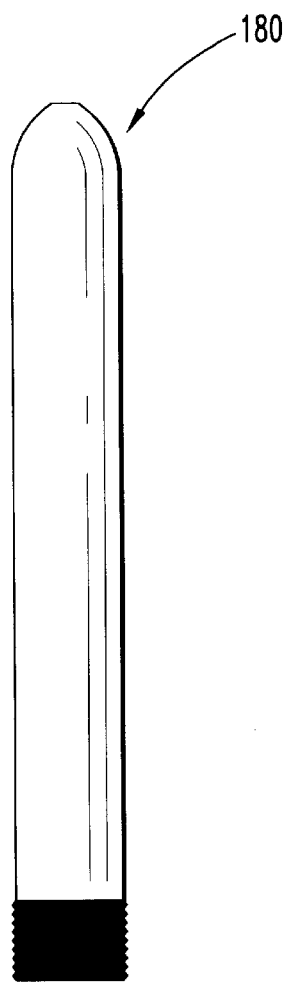
FIG. 25 is a side elevation view of a bone graft harvesting dilator.
Figure 26:
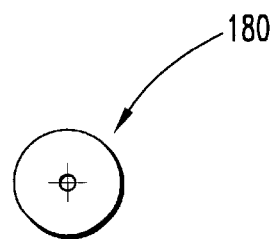
FIG. 26 is a cross-sectional view of the dilator shown in FIG. 25 taken along lines 26—26.
Figure 27:
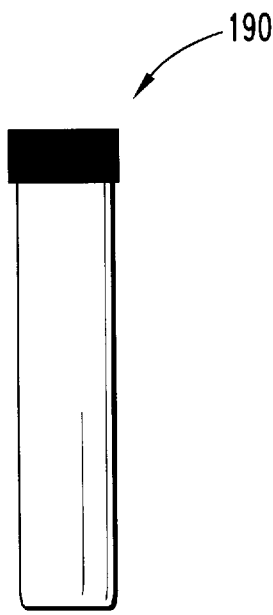
FIG. 27 is a side elevational view of a bone graft harvesting cannula.
Figure 28:
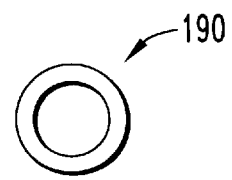
FIG. 28 is a top view of the bone graft harvesting cannula shown in FIG. 27.

Autograft can be harvested from locations such as the iliac crest using drills, gouges, curettes and trephines and other tools and methods which are well known to surgeons in this field. In one embodiment, autograft is harvested from the iliac crest with a minimally invasive donor surgery. In this procedure, an awl 130 (FIG. 22) and then a blunt probe 160 (FIG. 23) is inserted through a small incision to the donor location such as the iliac crest. A guide pin 170 (FIG. 24) is inserted through the incision next to the probe 160. The probe is removed and a cannulated dilator 180 (FIGS. 25–26) is inserted over the pin 170. A bone graft harvesting cannula 190 (FIGS. 27 and 28) is then inserted over the dilator 180.

The osteogenic compositions used in this invention preferably comprise a therapeutically effective amount of a bone inductive factor such as a bone morphogenetic protein in a pharmaceutically acceptable carrier. The preferred osteoinductive factors are the rhBMPs. Most preferably, the bone morphogenetic protein is a recombinant human BMP-2. However, any bone morphogenetic protein is contemplated including bone morphogenetic proteins designated as BMP-1 through BMP-13. BMPs are commercially available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. W093/00432 to Wozney et al.; WO94/26893 to Celeste et al.; and W094/26892 to Celeste et al.

The use of synthetic or recombinant osteoinductive proteins or factors such as recombinant human bone morphogenetic proteins with this invention is particularly advantageous because they avoid the disadvantages of both autograft and allograft and may increase the chances fo achieving a successful fusion. Furthermore, this invention makes the use of osteoinductive proteins safer by preserving a natural tissue barrier between the fusion site nad the epidural space. The safety of growth factors in the spinal canal, intra-pleural or intra-peritoneal cavities, or retroperitoneum has not yet been demonstrated. The possibility of such complication as adhesions, arachnoiditis, retroperitoneal fibrosis, etc. must be excluded before human use will be feasible. This inventive endo-surgical approach traverses no vital structures and so the risk of exposure of these structures is minimized and possibly eliminated.

The choice of carrier material for the osteogenic composition is based on biocompatibility, biodegradability, mechanical properties and interface properties. The particular application of the compositions of the invention will define the appropriate formulation. The carrier may be any suitable carrier capable of delivering the proteins to the intertransverse interval T. Most preferably, the carrier is capable of being eventually resorbed into the body. One preferred carrier is an absorbable collagen sponge marketed by Integra LifeSciences Corporation under the trade name Helistat® Absorbable Collagen Hemostatic Agent. Another preferred carrier is an open cell polylactic acid polymer (OPLA). Other potential matrices for the compositions may be biodegradable and chemically defined calcium sulfate, tricalcium phosphate (TCP), hydroxyapatite (HA) and polyanhydrides. Other potential materials are biodegradable and biologically well defined, such as bone or dermal collagen. Further matrices are comprised of pure proteins or extracellular matrix components. The osteoinductive material may also be an admixture of BMP and a polymeric acrylic ester carrier, such as polymethylmethacrylic.

The most preferred carrier is a biphasic calcium phosphate ceramic. Hydroxyapatite/tricalcium phosphate ceramics are preferred because of their desirable degradation rates in vivo. Any size or shape ceramic carrier which will fit into the fusion site is contemplated. Rectangular blocks are commercially available from Sofamor Danek Group, B. P. 4-62180 Rang-du-Fliers, France and Bioland, 132 Route d:Espagne, 31100 Toulouse, France. In one specific embodiment the carrier was a rectangular block measuring 1.4 cm×1.2 cm×4.0 cm. Of course, cylindrical and other suitable shapes are contemplated. The osteoinductive factor is introduced into the carrier in any suitable manner. For example, the carrier may be soaked in a solution containing the factor.

The present invention also provides several specialized instruments for minimally invasive surgery. The self-retaining retractor 30 depicted in FIGS. 6 and 7 includes two curved elongated portions 31, 32 attached with a fastener 45 at a pivot point 33. Manual gripping portions 34, 35 are attached to one end 36, 37 of each of the elongated portions 31, 32. The retractor includes means for varying and securing the distance between the second ends of the elongated portions 31, 32 for retracting skin. In one embodiment, the means includes a ratchet bar 43, pawl lever 44 that engages the bar 43 and leaf spring 45 that biases the lever 44 against the bar 43. Skin gripping teeth 40 are provided at the second end 41 of each of the elongated portions. In one embodiment, the retractor 30 is provided with five teeth 40, three on one portion 31 and two on the other 32. The teeth 40 are oriented at an angle $\alpha_1$ of about 90 degrees which facilitates engagement and retraction of the tissue.

This invention also contemplates a novel endosurgical retractor 50 as depicted in FIGS. 8 and 9. The endosurgical retractor 50 includes a retraction portion 51, a curved shaft 56 and a gripping portion 59. The curved shaft 56 includes a proximal end 57 attached to the gripping portion 59 and a distal end 58 attached to the second end 53 of the retraction portion 51. The shaft 56 includes a bend 56a defining an arc subtending an angle $\alpha_2$ of at least about 120 degrees. In a most preferred embodiment, the angle $\alpha_2$ is about 160 degrees. The shaft 56 also preferably includes a second bend 56b which bends the handle 56 in a direction away from the retraction portion 51. The gripping portion 56, the bend 56b and the shaft 56 form an angle $\alpha_3$ which is at least about 90 degrees. Most preferably the angle $\alpha_3$ is about 110 degrees. One purpose of the bends 56a, 56b can be appreciated with reference to FIG. 3. In particular, the bends 56a, 56b allow the retraction portion 51 to be inserted into the channel 10 with the handle portion 59 outside the body and projecting conveniently posterior to the patient.

The retraction portion includes a first end 52 and a second end 53 with a flattened plate 54 between the first 52 and second 53 ends, as shown in FIG. 9. The flattened plate 54 is configured to atraumatically retract tissue to create a working space within an endosurgical site. Preferably the flattened plate 54 has a width $W_1$ which is greater than a diameter $D_1$ of the shaft 56. In a most preferred embodiment, the width $W_1$ is about three times greater than the diameter $D_1$. In one specific embodiment the plate 54 has a width $W_1$ of 1.5 cm and a length $L_1$ of 3.5 cm. The first end 52 can include an edge 55 for engaging tissue. The edge 55 is preferably curved toward the gripping portion 59 and forms an angle $\alpha_4$ which is between 90 degrees and 150 degrees (FIG. 8 Most preferably the angle $\alpha_4$ is about 135 degrees.

The gripping portion 59 is configured for manually gripping and manipulating the device 50. Preferably, the gripping portion 59 includes a gripping surface 59a such as knurlings. Alternatively, the gripping portion 59 may include an ergonomic handle having cut out portions sized to receive a surgeon's fingers.

The endosurgical elevator 60 shown in FIGS. 10–12 includes a thin, flat rounded working end 61, a thin round, shaft 62, and an ergonomic handle 63. The working end 61 is configured to gently dissect muscle from fascia in the procedures of this invention. The working end 61 in one specific embodiment is 0.8 cm×2.0 cm. The handle 63 is provided with cut-out portions 64 which are sized and shaped to accommodate the surgeon's fingers to facilitate gripping and manipulating the elevator 60. Preferably, the handle 63 also includes a gripping surface 63a such as knurlings. The shaft 62 also includes a bent region 65 or a pair of bends each forming an angle $\alpha_5$ and $\alpha_6$ of at least 90 degrees and preferably about 135 degrees. The elevator 50 is configured to fit into the channel 10 without the surgeon's hands blocking the working area. Most preferably the bent region 65 is provided with a concave finger pusher 66 shown in detail in FIG. 12B. The finger pusher 66 is configured to allow the surgeon to apply manual pressure for elevating tissue and directing the working end 61 of the instrument 60.

Figure 15:
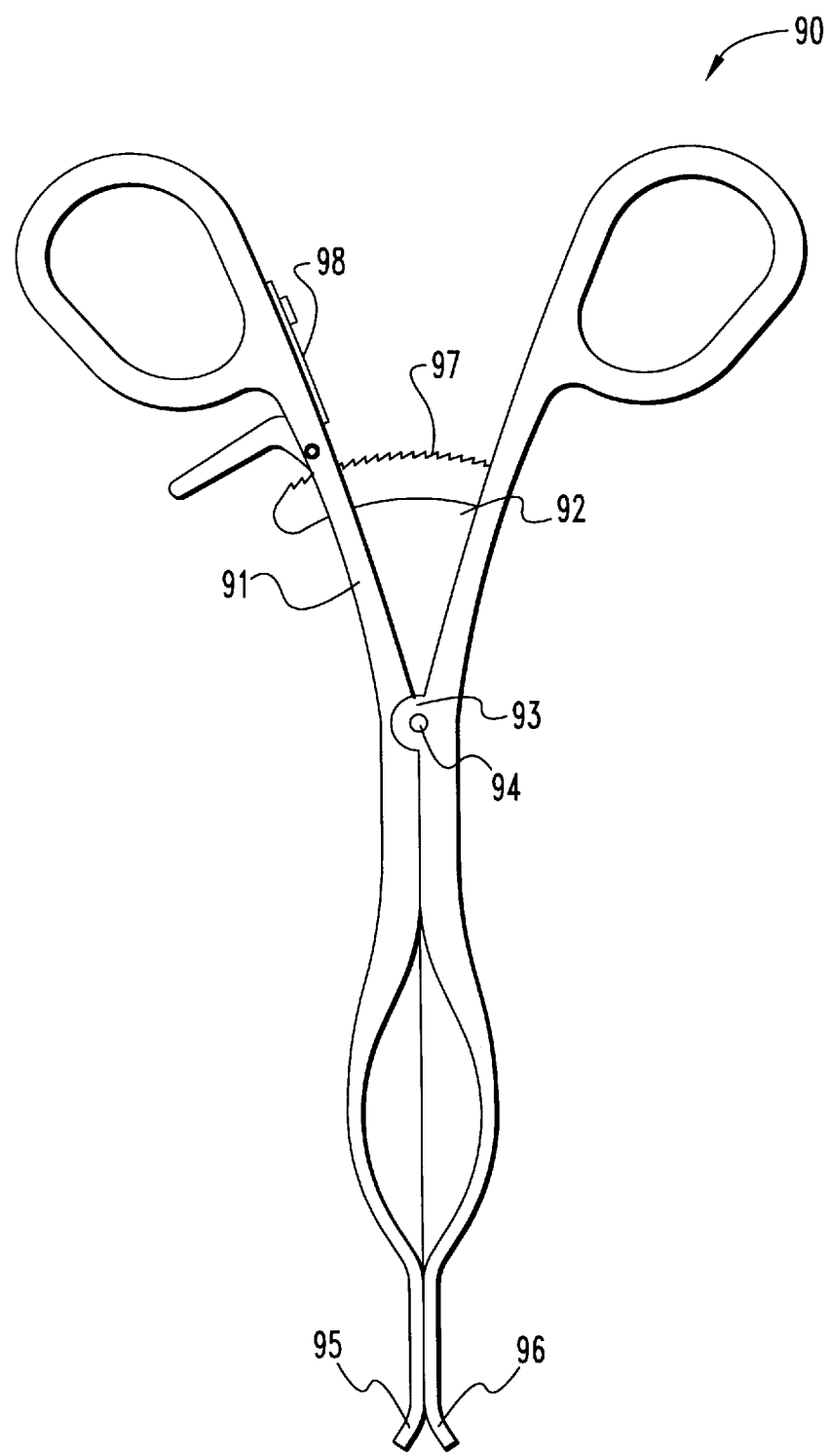
FIG. 15 is a top elevational view of a self-retaining endosurgical speculum provided by this invention.
Figure 16:
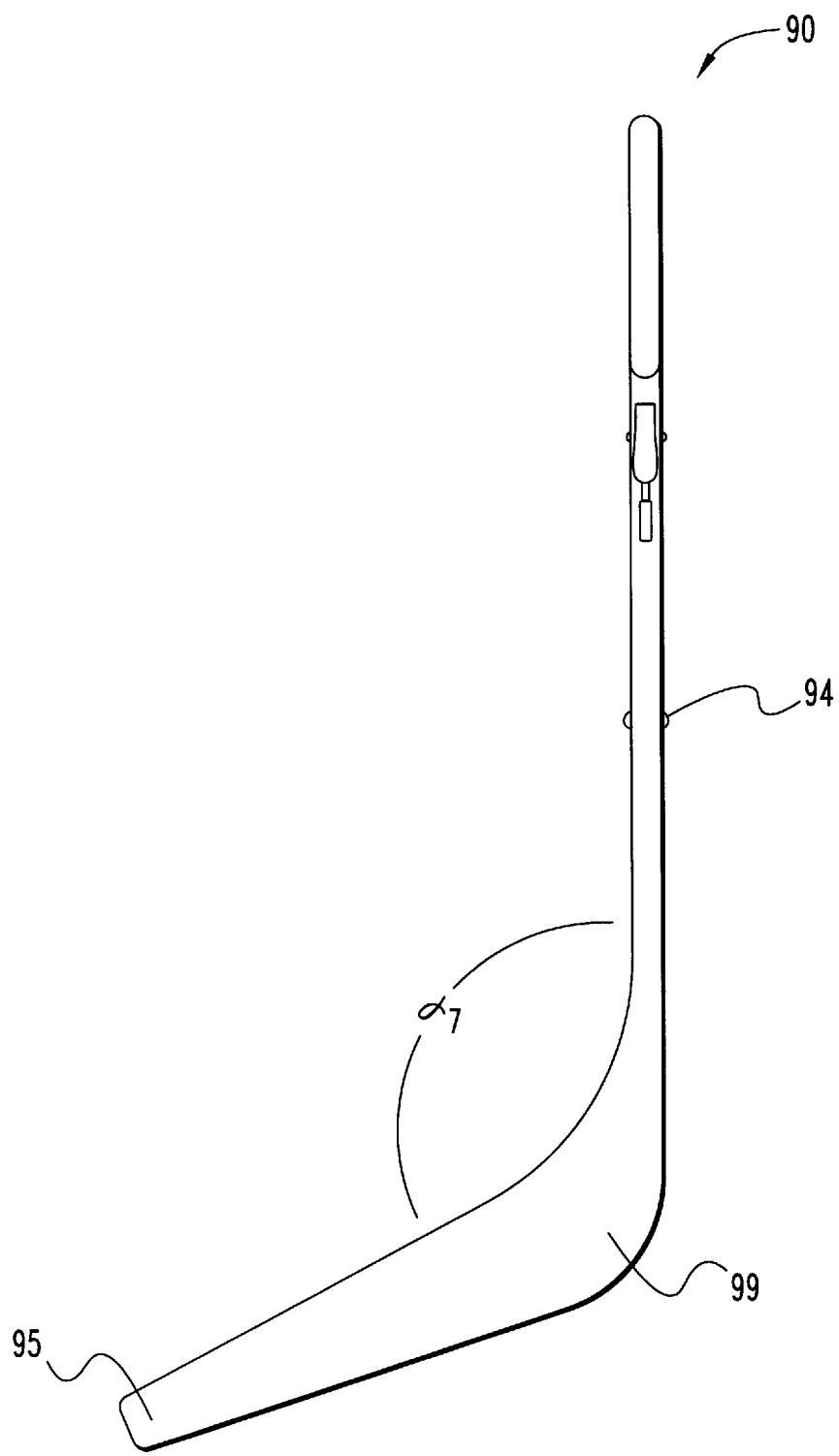
FIG. 16 is a side elevational view of the speculum shown in FIG. 15.

A self-retaining endosurgical speculum 90 is also provided and is depicted in FIGS. 15 and 16. The speculum 90 includes two curved elongated working arms 91, 92 attached at a pivot point 93 with a fastener 94. The speculum also includes means for varying and securing the distance between the working ends 95, 96 of the arms 91, 92. In one embodiment, the means includes a leaf spring closure mechanism 98 bearing against a rachet retention bar 97. The arms 91, 92 of speculum 90 each include a bend 99 which has an angle $\alpha_6$ of between about 80 degrees and 120 degrees. The bend 99, preferably about 110 degrees, is configured to allow the surgeon to comfortably operate the speculum and to keep the opposite end of the speculum 90 away from the incision so that the speculum 90 does not block vision or operation in the incision. In a specific embodiment, the working arms are 12 cm in length, with rounded, fluted ends, tapered to 1 cm in width.

Any suitable endoscope or other viewing device is contemplated for use in various steps of the inventive procedures. The device 100 depicted in FIGS. 17 and 18 includes an eye piece 101, a fiber optic light connector 102, a rod lens 103, a sheath 105 and a Luer Lock® connector. The rod lens 103 is preferably no longer than about 15 cm and is most preferably about 10 cm. Preferably the viewing angle $\alpha_8$ is at least about 30 degrees. The tip 107 of the sheath 105 preferably extends beyond the tip 104 of lens 103a distance of $L_2$ to protect the device from tissue fluid soiling.

Figure 21:
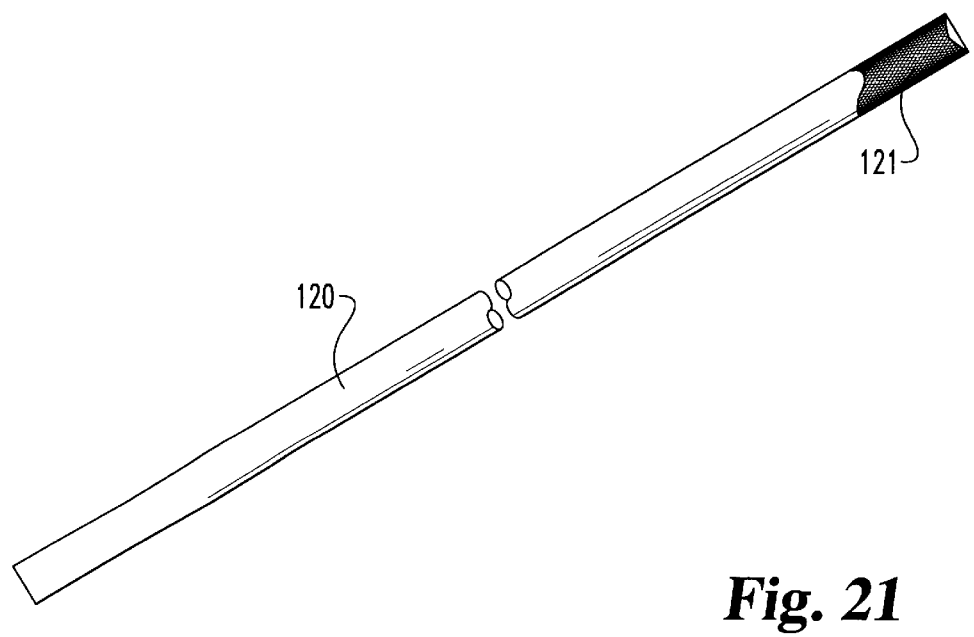
FIG. 21 is a graft delivery piston for use with the device depicted in FIG. 20.
Figure 20:
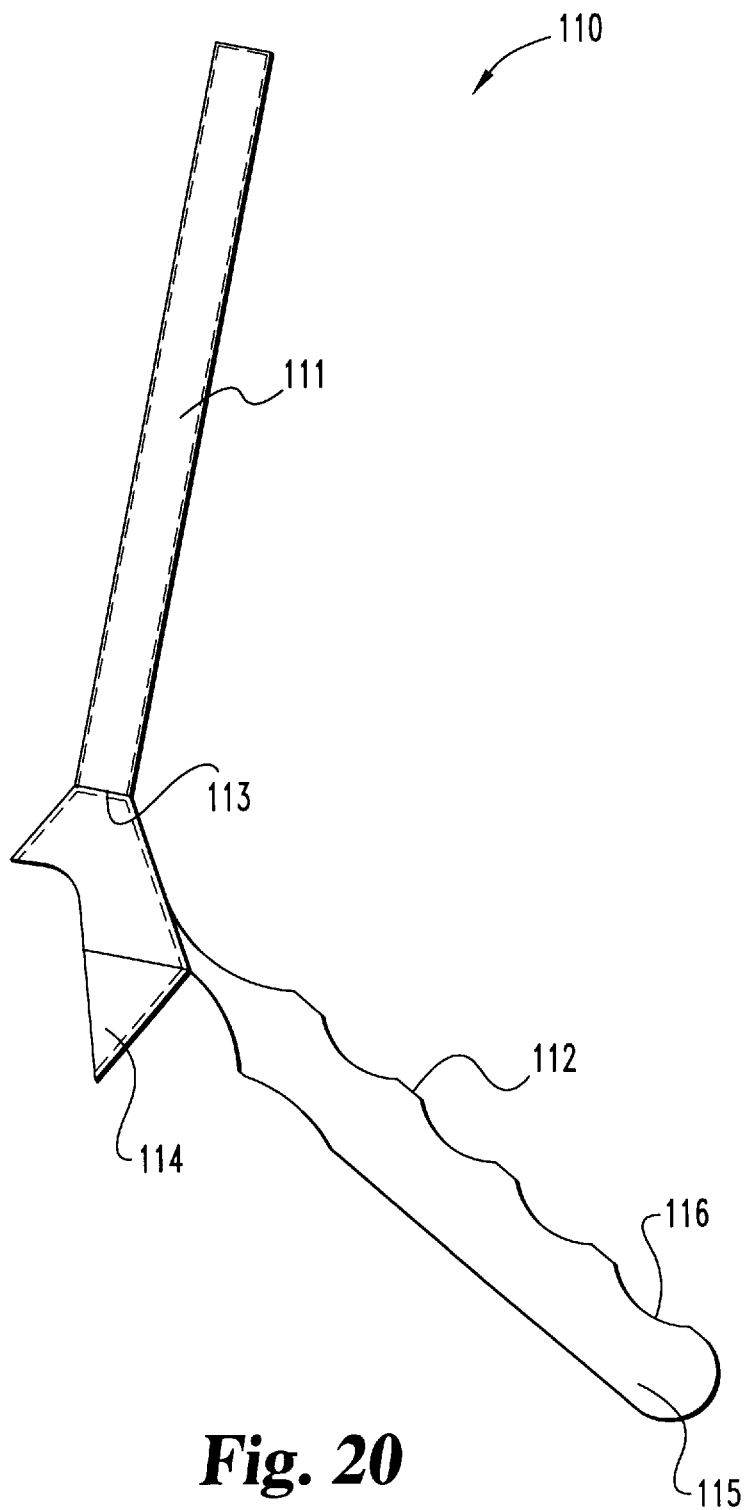
FIG. 20 is a side elevational view of a graft delivery device.

An endosurgical graft delivery assembly is shown in FIGS. 20 and 21 and includes an endosurgical graft delivery device 110 and a graft delivery piston 120. The graft delivery device includes a delivery cannula 111, a handle portion 112 and an opening 113 for receiving graft material into the cannula 111. Preferably, the opening 113 is surrounded by a funnel 114. Also, preferably the handle portion 112 includes a handle 115 with cut out portions 116 for a surgeon's fingers. In one embodiment the device 110 includes a 1.0 cm I.D. thin wall cannula, 15 cm in length. The funnel 114 is conical with a minor diameter of 1.0 cm and a major diameter=3.0 cm, length=2.0 cm), and an ergonomic handle. A graft delivery piston 120 (FIG. 21) is provided which is insertable within the cannula 111 for ejecting graft material from the cannula 111 and into the fusion site. The piston 120 is long enough to fully eject the graft material from the cannula 111 and preferably includes a knurled gripping portion 121. In one embodiment where the cannula 111 is about 15 cm, the piston 120 is about 30 cm in length.

Figure 23:
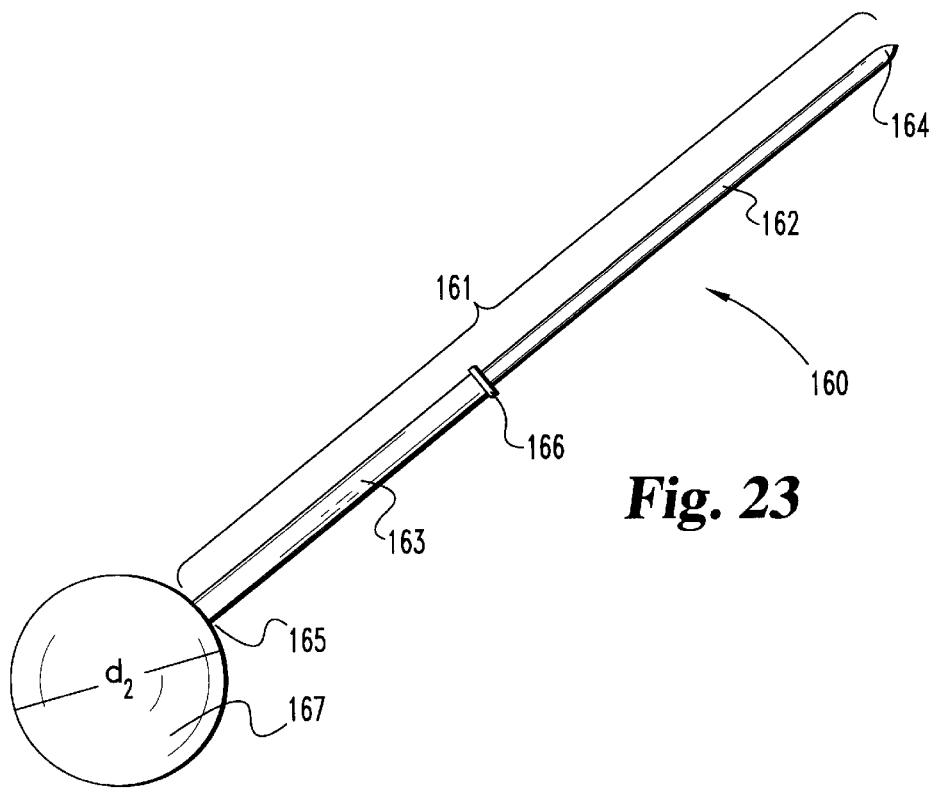
FIG. 23 is a side elevational view of a blunt probe provided by this invention.

A blunt probe 160 depicted in FIG. 23 is sized and configured to be accepted through a small donor incision for obtaining autograft. The probe 160 includes a small diameter rod 161 having a first portion 162 and a second portion 163. A smoothly tapered working end 164 is attached to the first portion 162 and a gripping portion 165 is attached to the second portion 163 of the rod 161. In a preferred embodiment the probe 160 includes a stop member 166 between the first 162 and second 163 portions for preventing the probe 60 from being inserted too deeply. The gripping portion 165 preferably includes a ball handle 167 which is configured to facilitate gripping and manipulating the device. In one specific embodiment, the probe 160 is a 0.3 cm diameter rod 161, with a first portion having a length of about 10 cm and a second portion having a length of about 7 cm and a ball handle 167 having a diameter $d_2$ of about 4 cm.

The following specific examples are provided for purposes of illustrating the invention, and no limitations on the invention are intended thereby.

EXAMPLES

Rabbit Model

Methods

Seven New Zealand white rabbits were examined at necropsy and during non-survival surgeries to determine the most convenient and safest access routes and to develop special instruments for video-assisted (VA) lateral intertransverse process arthrodesis.

Thirty-eight male skeletally mature (4/5–5 kg) New Zealand white rabbits underwent L4-L5 intertransverse process arthrodesis. The rabbits were divided into three groups: The "OPEN" group (n=16) underwent a standard open muscle-splitting approach using rhBMP-2/collagen as a bone graft substitute; the "VA-Control" group (N=6) underwent video-assisted lateral intertransverse process arthrodesis with the collagen implant only (no growth factor); and the "VA-BMP" group (n=16) underwent VA lateral intertransverse process arthrodesis with rhBMP-2/collagen as the graft material.

The open group received open dissection of the intertransverse interval for the purpose of graft material deposition. A single midline incision was made over the lumbosacral spine. Paraspinal muscles were elevated on each side to expose the transverse processes and the intertransverse membrane. The bone was decorticated with a high-speed burr. The wound was irrigated, graft material is placed in the intertransverse intervals and the wound is closed. The graft material included a bovine type 1 collagen sponge carrier (Genetics Institute, Cambridge Ma) was inserted as five rectangular pieces (15×30 mm each) for a total implant volume of 24 cc per fusion side. In the VA-BMP group, the collagen sponge was impregnated with 0.24 mg/fusion side of rhBMP-2 (Genetics Institute, Cambridge Ma). The BMP and carrier was delivered to the intertransverse interval using a 5 mm tube and plunger.

Both the VA-Control and VA-BMP groups received endosurgical dissection for the purpose of graft-substitute deposition. A small incision was made at the lateral border of the paraspinal muscles at the dorsal border of the external oblique muscle. A modified Love nerve root retractor was inserted into the compartment of the fascia, deep to the paraspinal muscles to create a working space for video assisted endoscopic visualization. A periosteal elevator was used to expose the transverse processes. An accessory portal was created for the decotication and graft insertion.

A bovine type 1 collagen sponge carrier (Genetics Institute, Cambridge Ma) was inserted as five rectangular pieces (15×30 mm each) for a total implant volume of 2.4 cc per fusion side. In the VA-BMP group, the collagen sponge was impregnated with 0.24 mg/fusion side of rhBMP-2 (Genetics Institute, Cambridge Ma). The BMP and carrier was delivered to the intertransverse interval using a 5 mm tube and plunger. After decortication of the exposed bone and the delivery of graft material, the wounds were closed. The procedure was repeated on the opposite side.

The animals were housed without restraint for ten weeks before examination. All animals were monitored daily for signs of neurologic impairment, infection, and general behavior.

Results

An expedient and neurovascularly safe, minimally invasive route to the intertransverse process interval was identified which was an intermuscular approach between the longissimus and multifidus muscles for the rabbit. All 32 rabbits in the OPEN and VA-BMP groups achieved solid intertransverse process lumbar fusions when blindly assessed at ten weeks by manual palpation, posteroanterior radiographs, computed tomography, and undecalcified histology. There were no neurological impairments nor any statistically significant difference between the two groups in frequency of postoperative infection or other complications. None of the animals in the VA-Control group showed evidence of intertransverse process fusion.

TABLE I

Results of Video-Assisted Lateral Intertransverse Process Arthrodesis Using a Minimally Invasive Fusion Technique in the Rabbit Model.

| Group[1] | Surgical Technique | Graft Material[2] | Fusions[3] |
|---|---|---|---|
| Open | Standard Open | Carrier + 0.24 mg BMP | 16/16 |
| VA-Control | Endo-surgical | Carrier alone | 0/6 |
| VA-BMP | Endo-surgical | Carrier + 0.24 mg BMP | 16/16 |

[1]The "OPEN" group (n = 16) underwent a standard open muscle-splitting approach using rhBMP-2/collagen as a bone graft substitute; the "VA-Control" group (N = 6) underwent video-assisted lateral intertransverse process arthrodesis with rhBMP-2/collagen as the graft material.
[2]A bovine type 1 collagen sponge carrier (Genetics Institute, Cambridge Ma) was inserted as five rectangular pieces (15 × 30 mm each) for a total implant volume of 2/4 cc per fusion side. In the Open and VA-BMP groups, the collagen sponge was impregnated with 0.24 mg/fusion side of rhBMP-2 (Genetics Institute, Cambridge Ma).
[3]Fusions blindly assessed at 10 weeks by manual palpation, posteroanterior radiographs, computed tomography and undecalcified histology.

Rhesus Monkey Model (Collagen Carrier)

Methods

Five rhesus monkeys were examined at necropsy and during non-survival surgeries to determine the most convenient and safest access routes and to develop special instruments for video-assisted (VA) lateral intertransverse process arthrodesis. Rhesus monkeys (n=4) underwent video-assisted lateral intertransverse process arthrodesis using rhBMP-2/collagen (32 mg/fusion side) following laminectomy of L4-5. All animals were monitored daily for signs of neurologic impairment, infection, and general behavior.

Results

Again, an expedient and neurovascularly safe, minimally invasive route to the intertransverse process interval was identified which was a lateral, extramuscular approach around the iliocostalis muscle for the rhesus monkey.

Exposure, decortication and grafting with rhBMP-2/collagen was successfully accomplished in all 4 monkeys through the minimally invasive approach (VA) without complication. Postoperative recovery was felt to be more rapid than previously observed in rhesus monkeys after the same procedures were performed through a conventional open surgical approach.

Rhesus Monkey Model (Ceramic Carrier)

Methods

Five rhesus monkeys were examined at necropsy and during non-survival surgeries to determine the most convenient and safest access routes and to develop special instruments for video-assisted (VA) lateral intertransverse process arthrodesis. Rhesus monkeys (n=5) underwent video-assisted lateral intertransverse process arthrodesis using rhBMP-2 (9mg/fusion side) in a Hydroxyapatite/Tricalcium phosphate ceramic carrier (12 mm×12 mm×40 mm) following laminectomy of L4-5. All animals were monitored daily for signs of neurologic impairment, infection, and general behavior.

Results

Again, an expedient and neurovascularly safe, minimally invasive route to the intertransverse process interval was identified which was a lateral, extramuscular approach around the iliocostalis muscle for the rhesus monkey.

Exposure, decortication and grafting with rhBMP-2-HA/TCP was successfully accomplished in all 5 monkeys through the minimally invasive approach (VA) without complication. Postoperative recovery was felt to be more rapid than previously observed in rhesus monkeys after the same procedures were performed through a conventional open surgical approach.

Discussion

The results of the rabbit and monkey tests show that the endo-surgical technique is equivalent or superior to open dissection for lumbar spine fusion as measured by solid fusion.

Cadaver Surgeries

A midline decompressive lumbar laminectomy was performed using conventional methods. After closure of the midline skin incision, a bilateral video assisted lateral intertransverse process arthrodesis was conducted through 2.5 cm transverse skin incisions centered over the lateral border of the paraspinal muscles. The thoraco-lumbar fascia was incised in the line of its fibers to expose the iliocostalis muscle. The 2 cm main working portal was established between the iliocostalis and the anterior layer of the thoraco-lumbar fascia where the tips of the target transverse processes were palpable. The attachments of the longissimus were separated from the thoraco-lumbar fascia in this case using the freer dissector. Periosteal elevation exposed each transverse processes in turn.

An accessory portal was established cephalad to the primary portal using a blunt probe. The sheath of the decorticating burr was introduced through the accessory portal over the blunt probe. With the burr in place and attached to a motorized hand piece, the transverse processes were decorticated in turn. In some cases, the decorticating burr was introduced through the primary wound along side the endoscope.

The graft material consisted of three sheets on collagen sponge impregnated with recombinant human bone morphogenetic protein 2 in a neutral buffered solution. The sheets of collagen sponge were allowed to stand for about 5 minutes and then stacked and rolled to expel excess liquid. The rolled cylinder of graft material was placed in a 1.2 cm plastic delivery cannula. The delivery cannula was inserted to the medial wall of the intertransverse process interval and the graft material was impelled into the wound using a Delrin rod. The growth factor impregnated collagen sponges were then distributed between the decorticated transverse processes to bridge the intertransverse process interval. The wounds were then closed with absorbable sutures and reinforcing skin staples. The entire procedure was completed within thirty minutes.

Human Surgeries

A midline decompressive lumbar laminectomy using conventional methods is performed on an anesthetized patient. After closure of the midline skin incision, a bilateral video assisted lateral intertransverse process arthrodesis is performed through 2.5 cm transverse skin incisions centered over the lateral border of the paraspinal muscles. The thoraco-lumbar fascia is incised in the line of its fibers to expose the iliocostalis muscle. A 2 cm main working portal is established between the iliocostalis and the anterior layer of the thoraco-lumbar fascia where the tips of the target transverse processes are palpable. The attachments of the longissimus are separated from the thoraco-lumbar fascia. Periosteal elevation exposed each transverse processes in turn. An accessory portal is established through a secondary incision cephalad to the primary portal using a blunt probe. The sheath of the decorticating burr is introduced through the accessory portal over the blunt probe. With the burr in place and attached to a motorized hand piece, the transverse processes are decorticated in turn. In some cases, the decorticating burr is introduced through the primary wound next to the endoscope.

The delivery cannula of a graft delivery assembly is loaded with graft material. The graft material is a biphasic hydroxyapatite/tricalcium phosphate ceramic block (1.4 cm×1.2 cm×4.0 cm) soaked with rh-BMP-2. The delivery cannula is inserted to the medial wall of the intertransverse process interval and the graft material is impelled into the fusion site using a graft delivery piston. The wounds are then closed with absorbable sutures and reinforcing skin staples.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. While the preferred embodiment discloses certain instruments, all suitable instruments are contemplated and others may even be preferred for use in the methods of this invention. For example, inserters are contemplated which accomodate different materials or configurations of the implant. A collagen sponge may require a different inserter than autograft.

In one specific example, an inserter 200 particularly suited for a ceramic implant is depicted in FIGS. 29 A–D. It is contemplated that this inserter 200 will compensate for the difficulty in insertion of certain bioceramics due to the brittleness of the material. The inserter shown in FIG. 29 includes a carrier element 205 and an obturator portion 210.

Figures 29A, 29B, 29C, 29D:
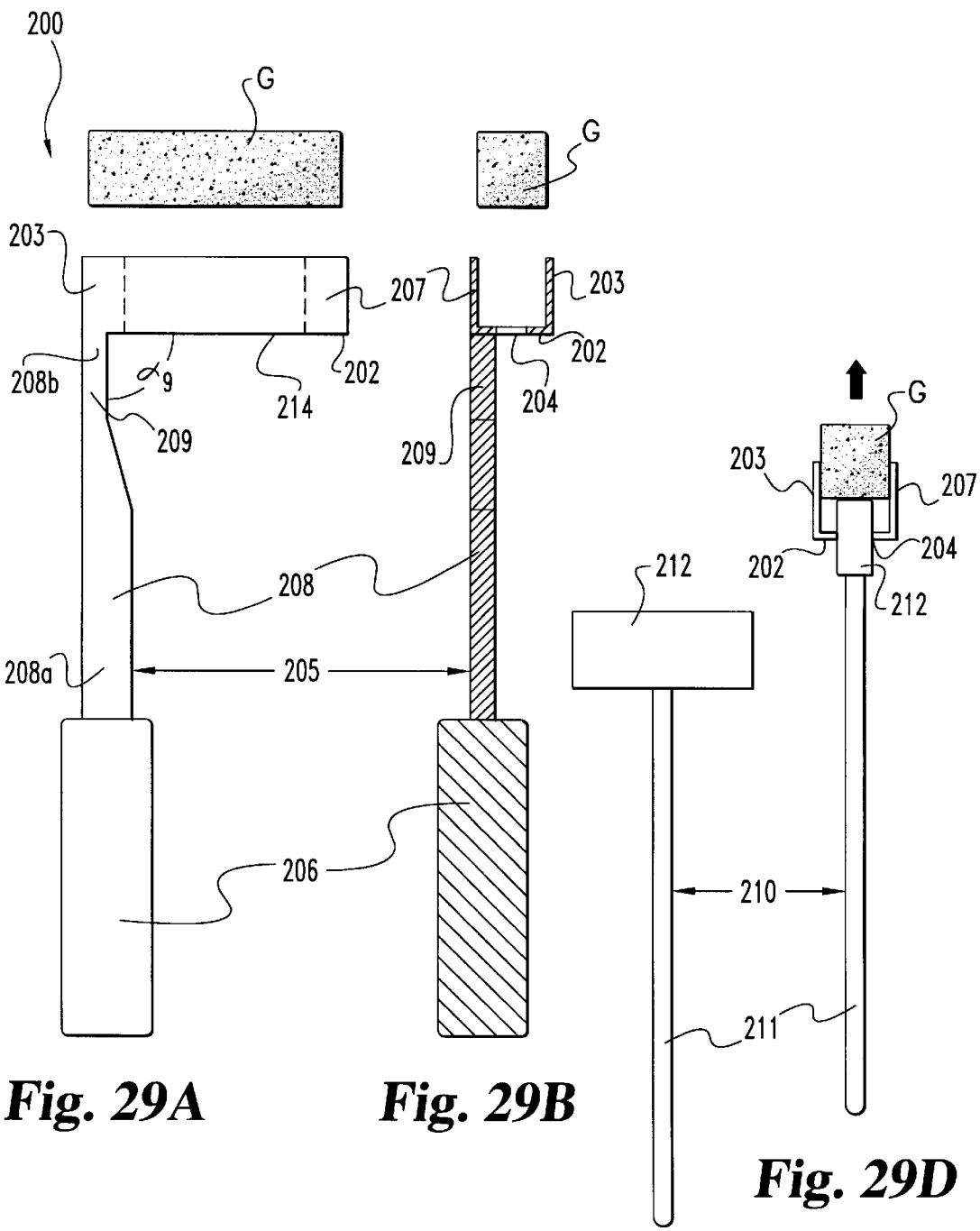
FIG. 29A is a side elevational view of the carrier element of an inserter provided by this invention.
FIG. 29B is a front longitudinal section of the carrier element shown in FIG. 29A.
FIG. 29C is a side elevational view of an obturator portion designed to operate with the carrier portion shown in FIG. 29A and B.
FIG. 29D is a front elevational view of the inserter of FIGS. 29A–C showing the obturator operating to expel an implant from the carrier element.

The carrier element 205 includes a handle 206 and a sheath 207, each connected to opposite ends 208a, 208b of a delivery shaft 208. The sheath 207 is configured to hold and protect an implant G, in particular a ceramic implant, during the insertion process. The sheath 207 also protects the intervening tissue from irritation as the implant passes to its destination. The sheath 207 preferably includes two side walls 203 connected by a seat 202 which defines an opening 204 for insertion of a portion of the obturator 210 for ejection of the implant G. The sheath 207 and the second end 208b of the shaft 208 preferably form an angle of about 90 degrees which properly orients the implant G for insertion at the fusion site. Referring to FIG. 29C, the obturator portion 210 includes a gripping portion 211 and an impacter 212. The impactor 212 includes an engaging surface 214 for engaging graft material or the implant G received within the sheath 207. The impactor 212 is sized to fit through the opening 214 of the carrier element 205 and eject the implant G from the sheath 207 as shown in FIG. 29D. The shaft 208 defines a narrowed portion 209 at one end 208b which provides space for the impactor 212 as the obturator portion 210 is assembled with the carrier element 205.

Although the inserter 200 is particularly suited to deliver ceramic graft materials to the intertransverse interval T according to the methods of this invention, the inserter 200 could be used in virtually any procedure where delivery of graft or graft substitutes is required.

Figure 30:
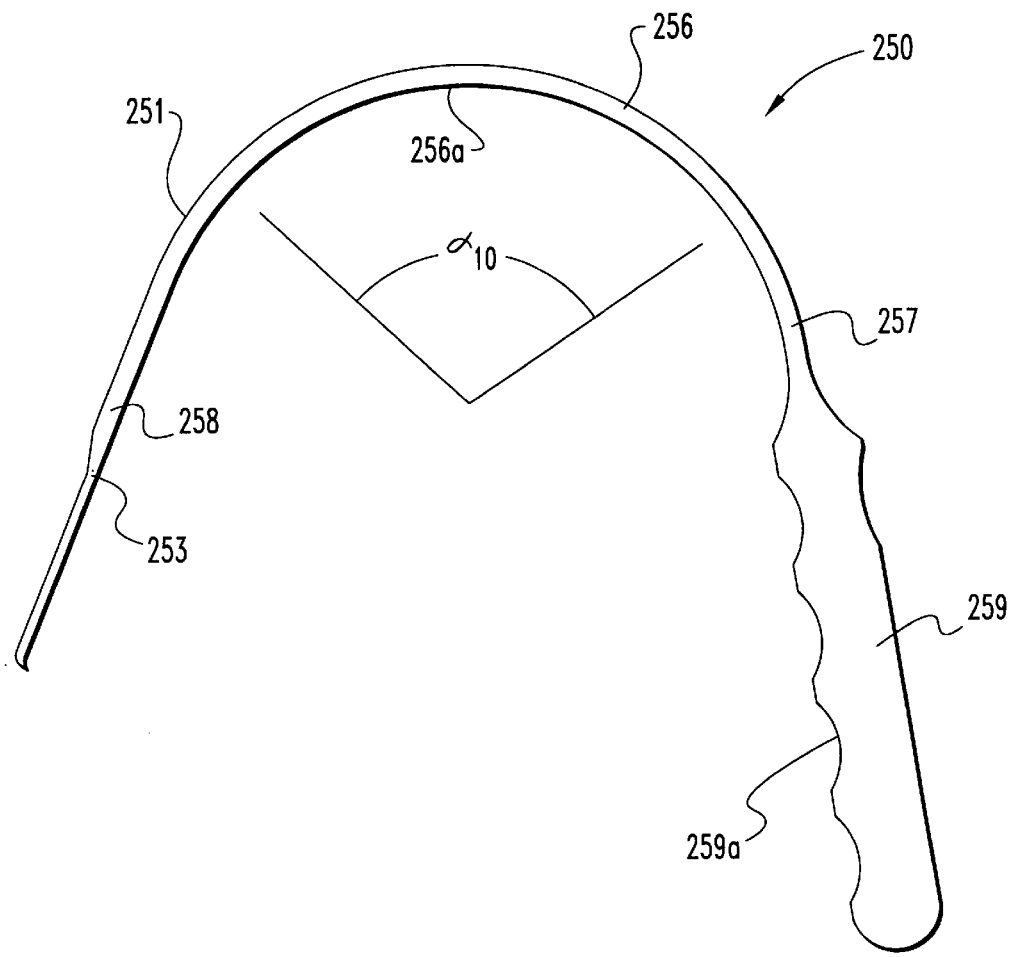
FIG. 30 is a side elevational view of an endosurgical retractor provided by this invention.

Another example of the modifications which this invention includes is shown in FIG. 30 which depict a substantially U-shaped endosurgical retractor 250. The retractor 250 includes a retraction portion 251, a curved shaft 256 and a gripping portion 259. The retraction portion 251 of this embodiment is identical to the retraction portion 51 of the retractor 50 shown in FIGS. 8 and 9. The gripping portion 259 preferably includes an ergonomic handle having cut out portions 259a sized to receive a surgeon's fingers.

The curved shaft 256 of the retractor 250 includes a proximal end 257 attached to the gripping portion 259 and a distal end 258 attached to the second end 253 of the retraction portion 251. The shaft 56 includes a bend 256a defining an arc subtending an angle $\alpha_{10}$ of at least about 120 degrees. In a most preferred embodiment, the angle $\alpha_{10}$ is about 160 degrees. One purpose of the bend 256a can be appreciated with reference to FIG. 3. In particular, the bend 256a allows the retraction portion 251 to be inserted into the channel 10 with the handle portion 259 outside the body and projecting conveniently posterior to the patient.

Therefore it will be understood by those of ordinary skill in the art that the methods of this invention can be accomplished with any suitable devices and that all variations which come within the scope of the following claims are desired to be protected.

What is claimed is:

1. An endosurgical device, comprising:
   a retraction portion having a first end and a second end and a flattened plate between said first and second ends, said first end including an edge for engaging tissue, said flattened plate configured to atraumatically retract tissue;
   a curved shaft having a proximal end and a distal end, said distal end attached to said second end of said retraction portion, said shaft having a first bend subtending an angle of at least about 120 degrees; and
   a gripping portion attached to said proximal end of said shaft, said gripping portion configured for manually gripping and manipulating the device;
   wherein said edge of said retraction portion forms a third angle with said flattened plate, said third angle being between about 90 and about 150 degrees.

2. The device of claim 1, wherein said first angle is about 160 degrees.

3. The device of claim 1 wherein said proximal end of said shaft includes a second bend, said second bend bending said gripping portion in a direction away from said retraction portion, said second bend, said gripping portion and said shaft forming a second angle of at least 90 degrees.

4. The device of claim 3 wherein said second angle is about 110 degrees.

5. The device of claim 1 wherein said third angle is about 135 degrees.

6. The device of claim 1 wherein said plate portion has a width that is greater than a diameter of said shaft.

7. The device of claim 6 wherein the width is about three times greater than the diameter.

8. The device of claim 6 wherein the width is about 1.5 cm and the plate has a length of about 3.5 cm.

9. The device of claim 1 wherein said gripping portion has a gripping surface with knurling.

10. An endosurgical device, comprising:
  a retraction portion having a first end and a second end and a flattened plate between said first and second ends, said first end including an edge for engaging tissue, said flattened plate configured to atraumatically retract tissue;
  a curved shaft having a proximal end and a distal end, said distal end attached to said second end of said retraction portion, said shaft having a first bend subtending a first angle of at least about 120 degrees; and
  a gripping portion attached to said proximal end of said shaft, said gripping portion configured for manually gripping and manipulating the device;
  wherein said plate has a width greater than a diameter of said shaft.

11. The device of claim 10 wherein the width is about three times greater than the diameter.

12. The device of claim 10 wherein the width is about 1.5 cm and the plate has a length of about 3.5 cm.

13. The device of claim 10 wherein said edge and said plate form a third angle, said third angle being in a range of about 90 to 150 degrees.

14. The device of claim 13 wherein said third angle is about 135 degrees.

15. The device of claim 10 wherein said first angle is about 160 degrees.

16. An endosurgical device, comprising:
  a retraction portion having a first end and a second end and a flattened plate between said first and second ends, said first end including an edge for engaging tissue, said flattened plate configured to atraumatically retract tissue;
  a curved shaft having a proximal end and a distal end, said distal end attached to said second end of said retraction portion, said shaft having a first bend subtending a first angle of at least about 120 degrees; and
  a gripping portion attached to said proximal end of said shaft, said gripping portion configured for manually gripping and manipulating the device;
  wherein said proximal end of said shaft includes a second bend forming a second angle between said shaft and said gripping portion of about 110 degrees to position said gripping portion in a direction away from said retraction portion.

17. The device of claim 16 wherein said first angle is about 160 degrees.

18. The device of claim 16 wherein said plate has a width that is greater than a diameter of said shaft.

19. The device of claim 16 wherein said edge and said plate form a third angle, said third angle being in a range of about 90 to 150 degrees.

20. The device of claim 16 wherein said gripping portion has a gripping surface with knurling.

* * * * *